US011389300B2

(12) United States Patent
Emerick et al.

(10) Patent No.: US 11,389,300 B2
(45) Date of Patent: Jul. 19, 2022

(54) STEMLESS SHOULDER IMPLANT WITH FIXATION COMPONENTS

(71) Applicant: Howmedica Osteonics Corp., Mahwah, NJ (US)

(72) Inventors: Bradley Grant Emerick, Columbia City, IN (US); Brian M. Strzelecki, Fort Wayne, IN (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 382 days.

(21) Appl. No.: 16/574,712

(22) Filed: Sep. 18, 2019

(65) Prior Publication Data
US 2020/0008947 A1    Jan. 9, 2020

Related U.S. Application Data

(62) Division of application No. 15/443,866, filed on Feb. 27, 2017, now Pat. No. 10,463,499.
(Continued)

(51) Int. Cl.
*A61F 2/40* (2006.01)
*A61B 17/86* (2006.01)
(Continued)

(52) U.S. Cl.
CPC ............ *A61F 2/4014* (2013.01); *A61B 17/86* (2013.01); *A61F 2/4003* (2013.01); *A61B 17/0401* (2013.01); *A61B 2017/044* (2013.01); *A61B 2017/0414* (2013.01); *A61F 2002/3069* (2013.01); *A61F 2002/3079* (2013.01);
(Continued)

(58) Field of Classification Search
CPC ......... A61F 2/40; A61F 2/4014; A61F 2/4003
See application file for complete search history.

(56) References Cited

U.S. PATENT DOCUMENTS

| 448,126 A | 3/1891 | Craig |
|---|---|---|
| 1,065,456 A | 6/1913 | Lowrey |

(Continued)

FOREIGN PATENT DOCUMENTS

| DE | 4220217 | 12/1993 |
|---|---|---|
| DE | 10233204 | 1/2004 |

(Continued)

OTHER PUBLICATIONS

Final Rejection issued in connection with U.S. Appl. No. 16/580,367, dated Aug. 24, 2021, 9 pages.
(Continued)

*Primary Examiner* — Jason-Dennis N Stewart
(74) *Attorney, Agent, or Firm* — Duane Morris LLP

(57) ABSTRACT

A humeral anchor assembly is provided that includes a humeral anchor and at least one screw. The humeral anchor is configured to form a part of or support a part of a shoulder prosthesis. The humeral anchor has a distal portion configured to be anchored in a proximal region of a humerus and a proximal portion. The proximal portion includes a proximal face configured to engage an articular component within a periphery thereof. The proximal portion also includes at least one aperture disposed adjacent to the periphery. The at least one screw is disposed through the at least one aperture. The screw has a first end portion engaged with the proximal portion of the anchor and a second end portion disposed in or through cortical bone of the humerus.

17 Claims, 21 Drawing Sheets

Related U.S. Application Data

(60) Provisional application No. 62/313,252, filed on Mar. 25, 2016.

(51) Int. Cl.
 *A61B 17/04* (2006.01)
 *A61F 2/30* (2006.01)

(52) U.S. Cl.
 CPC ............... *A61F 2002/30289* (2013.01); *A61F 2002/30784* (2013.01); *A61F 2002/30873* (2013.01); *A61F 2002/30884* (2013.01); *A61F 2002/30886* (2013.01); *A61F 2002/4007* (2013.01); *A61F 2002/4051* (2013.01); *A61F 2220/0016* (2013.01); *A61F 2250/006* (2013.01)

(56) References Cited

U.S. PATENT DOCUMENTS

| | | |
|---|---|---|
| 1,123,730 A | 1/1915 | Greenfield |
| 2,444,099 A | 6/1948 | Hennessey, Jr. |
| 2,886,081 A | 5/1959 | Cowley |
| 3,523,395 A | 8/1970 | Rutter et al. |
| 3,609,056 A | 9/1971 | Hougen |
| 3,738,217 A | 6/1973 | Walker |
| 4,042,980 A | 8/1977 | Swanson et al. |
| 4,147,464 A | 4/1979 | Watson et al. |
| 4,250,600 A | 2/1981 | Gunther |
| 4,261,062 A | 4/1981 | Amstutz et al. |
| 4,406,023 A | 9/1983 | Harris |
| 4,550,450 A | 11/1985 | Kinnett |
| 4,623,353 A | 11/1986 | Buechel et al. |
| 4,632,111 A | 12/1986 | Roche |
| 4,743,262 A | 5/1988 | Tronzo |
| 4,865,605 A | 9/1989 | Dines et al. |
| 4,883,491 A | 11/1989 | Mallory et al. |
| 4,919,670 A | 4/1990 | Dale et al. |
| 4,964,865 A | 10/1990 | Burkhead et al. |
| 4,986,833 A | 1/1991 | Worland |
| 5,026,373 A | 6/1991 | Ray et al. |
| 5,032,132 A | 7/1991 | Matsen et al. |
| 5,044,393 A | 9/1991 | Jiles |
| 5,080,673 A | 1/1992 | Burkhead et al. |
| 5,112,338 A | 5/1992 | Anspach, III |
| 5,163,964 A | 11/1992 | Lazzeri et al. |
| 5,171,277 A | 12/1992 | Roger |
| 5,257,995 A | 11/1993 | Umber et al. |
| 5,282,865 A | 2/1994 | Dong |
| 5,358,526 A | 10/1994 | Tornier |
| 5,489,309 A | 2/1996 | Lackey et al. |
| 5,489,310 A | 2/1996 | Mikhail |
| 5,507,817 A | 4/1996 | Craig et al. |
| 5,540,697 A | 7/1996 | Rehmann et al. |
| 5,658,290 A | 8/1997 | Lechot |
| 5,681,134 A | 10/1997 | Ebert |
| 5,702,486 A | 12/1997 | Craig et al. |
| 5,723,018 A | 3/1998 | Cyprien et al. |
| 5,776,194 A | 7/1998 | Mikol et al. |
| 5,800,551 A | 9/1998 | Williamson et al. |
| 5,810,524 A | 9/1998 | Wirth, Jr. et al. |
| 5,820,315 A | 10/1998 | Collard |
| 5,830,215 A | 11/1998 | Incavo et al. |
| 5,904,688 A | 5/1999 | Gilbert et al. |
| 5,954,727 A | 9/1999 | Collazo |
| 5,976,148 A | 11/1999 | Charpenet et al. |
| 6,045,582 A | 4/2000 | Prybyla |
| 6,063,124 A | 5/2000 | Amstutz |
| 6,099,214 A | 8/2000 | Lee et al. |
| 6,132,469 A | 10/2000 | Schroeder |
| 6,139,551 A | 10/2000 | Michelson et al. |
| 6,146,423 A | 11/2000 | Cohen et al. |
| 6,174,335 B1 | 1/2001 | Varieur et al. |
| 6,187,012 B1 | 2/2001 | Masini |
| 6,197,063 B1 | 3/2001 | Dews |
| 6,264,299 B1 | 7/2001 | Noda |
| 6,264,657 B1 | 7/2001 | Urbahns et al. |
| 6,306,171 B1 | 10/2001 | Conzemius |
| 6,364,910 B1 | 4/2002 | Shultz et al. |
| 6,368,271 B1 | 4/2002 | Sharratt |
| 6,368,353 B1 | 4/2002 | Arcand |
| 6,379,917 B1 | 4/2002 | Okun et al. |
| 6,409,730 B1 | 6/2002 | Green et al. |
| 6,508,840 B1 | 1/2003 | Rockwood, Jr. et al. |
| 6,520,994 B2 | 2/2003 | Nogarin |
| 6,537,278 B1 | 3/2003 | Johnson |
| 6,666,874 B2 | 12/2003 | Heitzmann et al. |
| 6,736,851 B2 | 5/2004 | Maroney et al. |
| 6,746,452 B2 | 6/2004 | Tuke et al. |
| 6,783,549 B1 | 8/2004 | Stone et al. |
| 6,786,684 B1 | 9/2004 | Ecker |
| 6,797,006 B2 | 9/2004 | Hodorek et al. |
| 7,044,973 B2 | 5/2006 | Rockwood, Jr. et al. |
| 7,097,663 B1 | 8/2006 | Nicol et al. |
| 7,140,087 B1 | 11/2006 | Giltner |
| 7,160,328 B2 | 1/2007 | Rockwood, Jr. et al. |
| 7,169,184 B2 | 1/2007 | Dalla Pria |
| 7,175,663 B1 | 2/2007 | Stone |
| 7,179,084 B1 | 2/2007 | Kometas |
| 7,189,036 B1 | 3/2007 | Watson |
| 7,189,261 B2 | 3/2007 | Dews et al. |
| 7,204,854 B2 | 4/2007 | Guederian et al. |
| 7,208,222 B2 | 4/2007 | Rolfe et al. |
| 7,344,565 B2 | 3/2008 | Seyer et al. |
| 7,465,319 B2 | 12/2008 | Tornier |
| 7,476,228 B2 | 1/2009 | Abou |
| 7,476,253 B1 | 1/2009 | Craig et al. |
| 7,585,327 B2 | 9/2009 | Winslow |
| 7,615,080 B2 | 11/2009 | Ondrla |
| 7,637,703 B2 | 12/2009 | Khangar et al. |
| 7,648,530 B2 | 1/2010 | Habermeyer et al. |
| 7,670,382 B2 | 3/2010 | Parrott et al. |
| 7,678,150 B2 | 3/2010 | Tornier et al. |
| 7,744,602 B2 | 6/2010 | Teeny et al. |
| 7,758,650 B2 | 7/2010 | Dews et al. |
| 7,887,544 B2 | 2/2011 | Tornier et al. |
| 7,927,376 B2 | 4/2011 | Leisinger et al. |
| D643,926 S | 8/2011 | Collins |
| 8,021,370 B2 | 9/2011 | Fenton et al. |
| 8,114,089 B2 | 2/2012 | Divoux et al. |
| 8,162,947 B2 | 4/2012 | Dreyfuss |
| 8,182,541 B2 | 5/2012 | Long et al. |
| 8,187,282 B2 | 5/2012 | Tornier et al. |
| 8,192,497 B2 | 6/2012 | Ondrla |
| 8,202,275 B2 | 6/2012 | Wozencroft |
| 8,221,037 B2 | 7/2012 | Neitzell |
| 8,231,682 B2 | 7/2012 | LaFosse |
| 8,246,687 B2 | 8/2012 | Katrana et al. |
| 8,277,512 B2 | 10/2012 | Parrott et al. |
| 8,317,871 B2 | 11/2012 | Stone et al. |
| 8,409,798 B2 | 4/2013 | Luy et al. |
| 8,419,798 B2 | 4/2013 | Ondrla et al. |
| D685,474 S | 7/2013 | Courtney |
| 8,500,744 B2 | 8/2013 | Wozencroft et al. |
| 8,506,638 B2 | 8/2013 | Vanasse et al. |
| 8,512,410 B2 | 8/2013 | Metcalfe et al. |
| 8,545,506 B2 | 10/2013 | Long et al. |
| 8,591,592 B2 | 11/2013 | Dreyfuss |
| 8,641,773 B2 | 2/2014 | Bergin et al. |
| 8,690,958 B2 | 4/2014 | Klawitter et al. |
| 8,702,800 B2 | 4/2014 | Linares et al. |
| 8,753,402 B2 | 6/2014 | Winslow et al. |
| 8,840,671 B2 | 9/2014 | Ambacher |
| 8,845,742 B2 | 9/2014 | Kusogullari et al. |
| 8,864,834 B2 | 10/2014 | Boileau et al. |
| 8,870,962 B2 | 10/2014 | Roche et al. |
| 8,876,908 B2 | 11/2014 | Katrana et al. |
| 8,882,845 B2 | 11/2014 | Wirth et al. |
| D745,678 S | 12/2015 | Courtney et al. |
| 9,233,003 B2 | 1/2016 | Roche et al. |
| 9,289,218 B2 | 3/2016 | Courtney, Jr. et al. |
| 9,326,865 B2 | 5/2016 | Katrana et al. |
| 9,498,345 B2 | 11/2016 | Brukhead, Jr. et al. |
| D840,539 S | 2/2019 | Courtney et al. |

(56) References Cited

U.S. PATENT DOCUMENTS

| | | |
|---|---|---|
| 10,456,264 B2 | 10/2019 | Hodorek et al. |
| 10,463,499 B2 | 11/2019 | Emerick et al. |
| 11,229,524 B2 | 1/2022 | Sperling |
| 2001/0034553 A1 | 10/2001 | Michelson et al. |
| 2001/0047210 A1 | 11/2001 | Wolf |
| 2002/0116007 A1 | 8/2002 | Lewis |
| 2002/0156534 A1 | 10/2002 | Grusin et al. |
| 2003/0004573 A1 | 1/2003 | Bagby |
| 2003/0028253 A1 | 2/2003 | Stone et al. |
| 2003/0031521 A1 | 2/2003 | Haughton et al. |
| 2003/0114933 A1 | 6/2003 | Bouttens et al. |
| 2003/0125810 A1 | 7/2003 | Sullivan et al. |
| 2004/0049270 A1 | 3/2004 | Gewirtz |
| 2004/0186586 A1 | 9/2004 | Seyer et al. |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0220674 A1 | 11/2004 | Pria |
| 2004/0243136 A1 | 12/2004 | Gupta et al. |
| 2004/0254646 A1 | 12/2004 | Stone et al. |
| 2005/0107882 A1 | 5/2005 | Stone et al. |
| 2005/0112397 A1 | 5/2005 | Rolfe et al. |
| 2005/0209597 A1 | 9/2005 | Long et al. |
| 2005/0261775 A1 | 11/2005 | Baum et al. |
| 2005/0267478 A1 | 12/2005 | Corradi et al. |
| 2006/0004378 A1 | 1/2006 | Raines |
| 2006/0009852 A1 | 1/2006 | Winslow et al. |
| 2006/0020344 A1 | 1/2006 | Shultz et al. |
| 2006/0064173 A1 | 3/2006 | Guederian |
| 2006/0089656 A1 | 4/2006 | Allard et al. |
| 2006/0142866 A1 | 6/2006 | Baratz et al. |
| 2006/0195105 A1 | 8/2006 | Teeny et al. |
| 2006/0200165 A1 | 9/2006 | Tulkis |
| 2006/0200249 A1 | 9/2006 | Beguin et al. |
| 2007/0010825 A1 | 1/2007 | Leisinger et al. |
| 2007/0100458 A1 | 5/2007 | Dalla Pria |
| 2007/0123890 A1 | 5/2007 | Way et al. |
| 2007/0123893 A1 | 5/2007 | O'Donoghue |
| 2007/0123909 A1 | 5/2007 | Rupp et al. |
| 2007/0156246 A1 | 7/2007 | Meswania et al. |
| 2007/0162141 A1 | 7/2007 | Dews et al. |
| 2007/0173945 A1 | 7/2007 | Wiley et al. |
| 2007/0212179 A1 | 9/2007 | Khangar et al. |
| 2007/0219562 A1 | 9/2007 | Slone et al. |
| 2007/0225817 A1 | 9/2007 | Reubelt et al. |
| 2007/0233132 A1 | 10/2007 | Valla |
| 2008/0021564 A1 | 1/2008 | Gunther |
| 2008/0077146 A1 | 3/2008 | Pernsteiner et al. |
| 2008/0195111 A1 | 8/2008 | Anderson |
| 2008/0249577 A1 | 10/2008 | Dreyfuss |
| 2009/0171462 A1 | 7/2009 | Poncet et al. |
| 2009/0281630 A1 | 11/2009 | Delince et al. |
| 2009/0306782 A1 | 12/2009 | Schwyzer |
| 2010/0042214 A1 | 2/2010 | Nebosky et al. |
| 2010/0087927 A1 | 4/2010 | Roche et al. |
| 2010/0114326 A1 | 5/2010 | Winslow et al. |
| 2010/0191340 A1 | 7/2010 | Dreyfuss |
| 2010/0274360 A1 | 10/2010 | Gunther |
| 2010/0278601 A1 | 11/2010 | Beynon |
| 2011/0153023 A1 | 6/2011 | Deffenbaugh et al. |
| 2011/0224673 A1 | 9/2011 | Smith |
| 2011/0276144 A1 | 11/2011 | Wirth et al. |
| 2011/0313533 A1 | 12/2011 | Gunther |
| 2012/0022664 A1 | 1/2012 | Vandermeulen et al. |
| 2012/0109321 A1 | 5/2012 | Stone et al. |
| 2012/0184964 A1 | 7/2012 | Hudak, Jr. et al. |
| 2012/0221111 A1 | 8/2012 | Burkhead, Jr. et al. |
| 2012/0265315 A1 | 10/2012 | Kusogullari et al. |
| 2012/0277880 A1 | 11/2012 | Winslow et al. |
| 2012/0296435 A1 | 11/2012 | Ambacher |
| 2013/0018476 A1 | 1/2013 | Katrana et al. |
| 2013/0123929 A1 | 5/2013 | McDaniel et al. |
| 2013/0123930 A1 | 5/2013 | Burt |
| 2013/0150972 A1 | 6/2013 | Iannotti et al. |
| 2013/0173006 A1 | 7/2013 | Duport |
| 2013/0178943 A1 | 7/2013 | Duport |
| 2013/0190882 A1 | 7/2013 | Humphrey |
| 2013/0211539 A1 | 8/2013 | McDaniel et al. |
| 2013/0261626 A1 | 10/2013 | Chavarria et al. |
| 2013/0261629 A1 | 10/2013 | Anthony et al. |
| 2013/0261754 A1 | 10/2013 | Anthony et al. |
| 2013/0282129 A1 | 10/2013 | Phipps |
| 2014/0012272 A1 | 1/2014 | Leisinger |
| 2014/0012380 A1 | 1/2014 | Laurence et al. |
| 2014/0058523 A1 | 2/2014 | Walch et al. |
| 2014/0074246 A1 | 3/2014 | Huebner et al. |
| 2014/0107792 A1 | 4/2014 | Hopkins et al. |
| 2014/0156012 A1 | 6/2014 | Winslow |
| 2014/0236304 A1 | 8/2014 | Hodorek et al. |
| 2014/0257499 A1 | 9/2014 | Winslow et al. |
| 2014/0296988 A1 | 10/2014 | Winslow et al. |
| 2014/0358239 A1 | 12/2014 | Katrana et al. |
| 2014/0358240 A1 | 12/2014 | Katrana et al. |
| 2014/0379089 A1 | 12/2014 | Bachmaier |
| 2015/0134066 A1 | 5/2015 | Bachmaier |
| 2015/0250601 A1 | 9/2015 | Humphrey |
| 2015/0289984 A1 | 10/2015 | Budge |
| 2015/0297354 A1 | 10/2015 | Walch et al. |
| 2016/0051367 A1 | 2/2016 | Gervasi et al. |
| 2016/0157911 A1 | 6/2016 | Courtney, Jr. et al. |
| 2016/0324648 A1 | 11/2016 | Hodorek et al. |
| 2017/0105843 A1 | 4/2017 | Britton et al. |
| 2017/0273800 A1 | 9/2017 | Emerick et al. |
| 2017/0304063 A1 | 10/2017 | Hatzidakis et al. |
| 2017/0367836 A1 | 12/2017 | Cardon et al. |
| 2019/0159906 A1 | 5/2019 | Knox et al. |
| 2019/0175354 A1 | 6/2019 | Knox et al. |
| 2019/0216518 A1 | 7/2019 | Courtney, Jr. et al. |

FOREIGN PATENT DOCUMENTS

| | | |
|---|---|---|
| DE | 102004042502 | 3/2006 |
| EP | 0 274 094 | 8/1990 |
| EP | 1 413 265 | 4/2004 |
| EP | 0 959 822 | 5/2004 |
| EP | 1 125 565 | 12/2004 |
| EP | 1 518 519 | 3/2005 |
| EP | 1 004 283 | 5/2005 |
| EP | 1 639 967 | 3/2006 |
| EP | 1 762 191 | 3/2007 |
| EP | 1 952 788 | 8/2008 |
| EP | 1 867 303 | 9/2010 |
| EP | 1 977 720 | 1/2011 |
| EP | 1 550 420 | 2/2012 |
| EP | 2 261 303 | 11/2012 |
| EP | 1 706 074 | 12/2012 |
| EP | 2 564 814 | 3/2013 |
| EP | 2 567 676 | 3/2013 |
| EP | 2 574 313 | 4/2013 |
| EP | 2 616 013 | 7/2013 |
| EP | 2 474 288 | 9/2013 |
| EP | 2 663 263 | 5/2014 |
| EP | 2 502 605 | 8/2014 |
| EP | 2 800 541 | 11/2014 |
| EP | 2 815 726 | 8/2015 |
| EP | 2 353 549 | 6/2016 |
| EP | 3 117 801 | 1/2017 |
| EP | 2 965 720 B1 | 7/2017 |
| FR | 2 674 122 | 9/1992 |
| FR | 2997290 B1 | 11/2015 |
| JP | 2009523578 A | 6/2009 |
| WO | WO 01/67988 | 9/2001 |
| WO | WO 02/17822 | 3/2002 |
| WO | WO 2008/011078 | 1/2008 |
| WO | WO 2008/146124 | 12/2008 |
| WO | WO 2011/081797 | 7/2011 |
| WO | WO 2012/035263 | 3/2012 |
| WO | WO 2012/130524 | 10/2012 |
| WO | WO 2013/009407 | 1/2013 |
| WO | WO 2013/064569 | 5/2013 |
| WO | WO 2013/148229 | 10/2013 |
| WO | WO 2014/005644 | 1/2014 |

(56) References Cited

FOREIGN PATENT DOCUMENTS

| WO | WO 2014/058314 | 4/2014 |
| WO | WO 2015/112307 | 7/2015 |
| WO | 2016094739 A1 | 6/2016 |
| WO | WO2016094739 A1 | 6/2016 |
| WO | WO 2017/165090 | 9/2017 |
| WO | WO 2017/184792 | 10/2017 |
| WO | WO 2018/022227 | 2/2018 |
| WO | WO 2019/060780 | 3/2019 |

OTHER PUBLICATIONS

Final Rejection issued in connection with U.S. Appl. No. 16/249,720, dated Aug. 20, 2021, 40 pages.

Non-Final Office Action issued in connection with U.S. Appl. No. 16/519,937, dated Aug. 17, 2021, 21 pages.

Barth, et al., "Is global humeral head offset related to intramedullary canal width? A computer tomography morphometric study," Journal of Experimental Orthopaedics, 2018, vol. 5, pp. 1-8.

Boileau, et al., "The Three-Dimensional Geometry of the Proximal Humerus: Implications for Surgical Technique and Prosthetic Design," J Bone Joint Surg, Sep. 1997, vol. 79-B, Issue 5, pp. 857-865.

Routman, et al., "Reverse Shoulder Arthroplasty Prosthesis Design Classification System," Bulletin of the Hospital for Joint Diseases, 2015, vol. 73 (Suppl 1), pp. S5-S14.

Final Rejection issued in connection with U.S. Appl. No. 16/208,956, dated Apr. 30, 2021, 13 pages.

Non-Final Office Action issued in connection with U.S. Appl. No. 17/250,964, dated Jul. 26, 2021, 27 pages.

Final Rejection issued in connection with U.S. Appl. No. 17/250,964, dated Sep. 9, 2021, 22 pages.

Non-Final Office Action issued in connection with U.S. Appl. No. 17/250,964, filed Feb. 24, 2022, 12 pages.

First Office Action issued in connection with Japanese Patent Application No. 2019-555151, dated Feb. 21, 2022, 5 pages.

Non-Final Office Action issued in connection with U.S. Appl. No. 16/648,128, filed Mar. 28, 2022, 15 pages.

Office Action issued in connection with Japanese Patent Application No. 2021-518159, dated May 24, 2022, 5 pages.

Third Examination Report issued in connection with Australian Patent Application No. 2019355854, dated May 10, 2022, 4 pages.

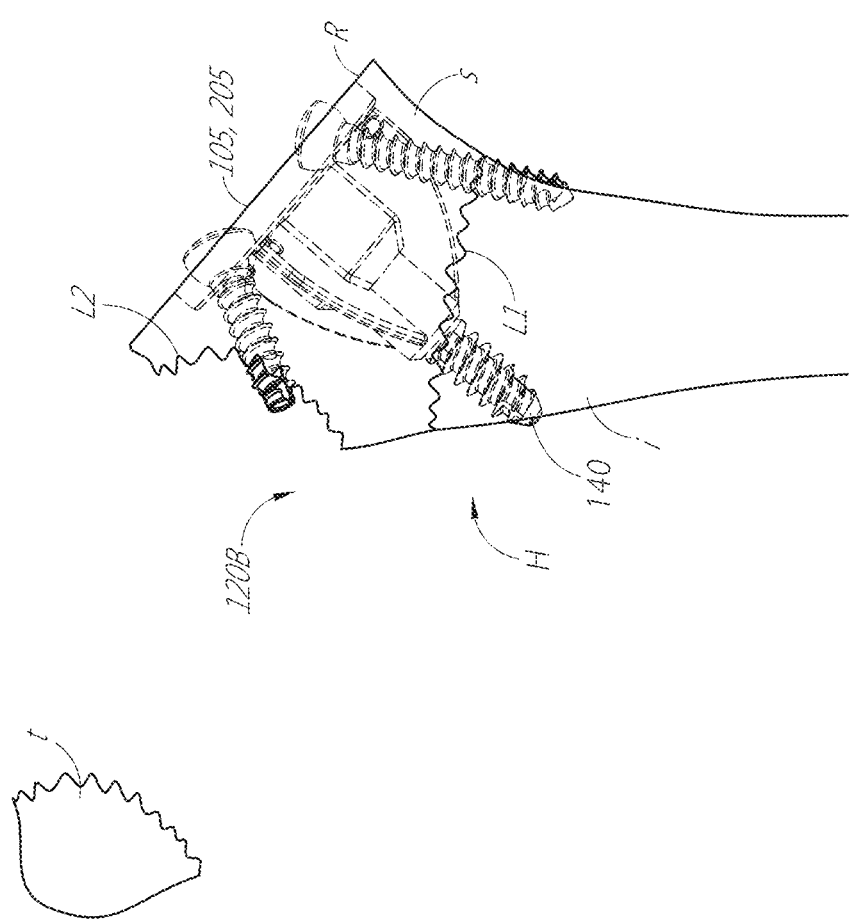

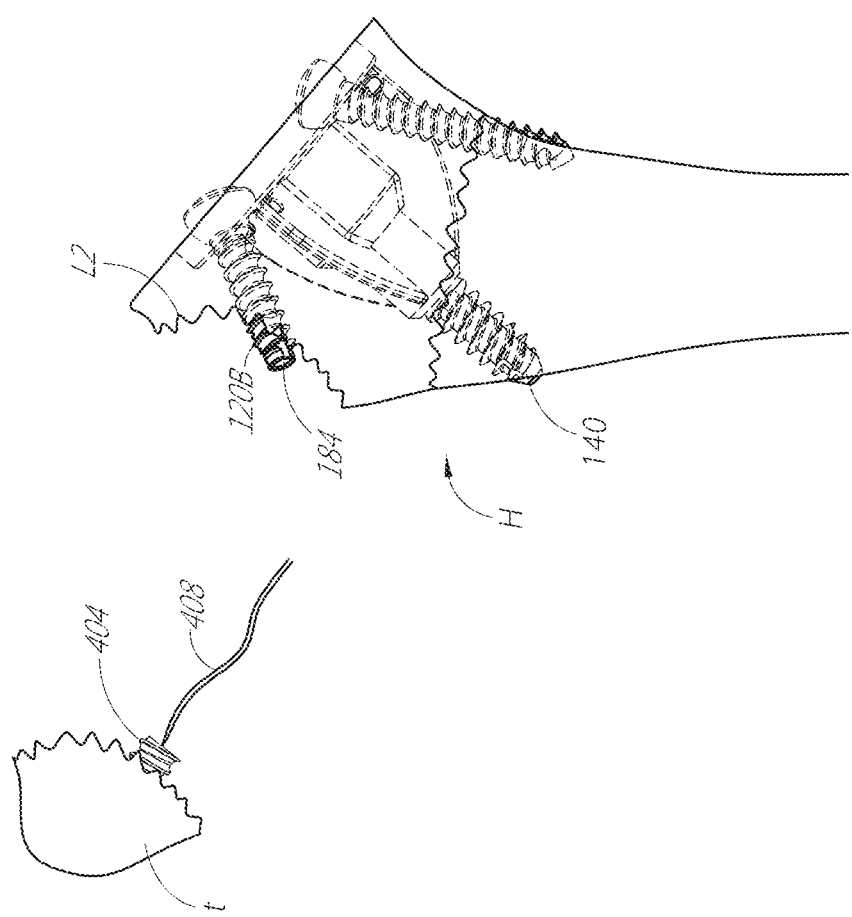

STEMLESS SHOULDER IMPLANT WITH FIXATION COMPONENTS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. § 1.57.

BACKGROUND OF THE INVENTION

Field of the Invention

The present disclosure relates to a stemless humeral component of a shoulder joint prosthesis.

Description of the Related Art

In a shoulder joint, the head of the humerus interacts with the glenoid cavity of the scapula in a manner similar to a "ball and socket" joint. Over time, it may become necessary to replace the shoulder joint with a prosthetic shoulder joint including a humeral component.

Traditionally, the humeral component includes a humeral head and a stem. The stem is configured to be inserted into an intramedullary canal of the humerus. In certain cases, insertion of the stem disadvantageously requires bone to be removed to fit the stem to the canal due to patient-to-patient anatomical variation. Another disadvantage of this approach is that integration of the stem into the bone through a natural process of bone ingrowth can make it difficult to remove the humeral component if it becomes necessary to replace the humeral component with another device. Due to the length of the stem it can be required to remove a lot of bone to facilitate removal of the stem; this complicates the ability to anchor a revision stem into the remaining bone.

A stemless humeral component may be used to address some of the disadvantages of conventional humeral components. Stemless humeral components can decrease the amount of bone loss when preparing the humerus to receive the component and decrease the complexity of the joint replacement procedure. Stemless humeral component designs can be more challenging to secure to the humerus. Conventional stemless designs rely on bone ingrowth for retention in the humerus. While such designs perform well over time, there is a risk in the early days and weeks after surgery where such ingrowth has not yet occurred that the stemless humeral component will be dislodged from the humerus. Dislodgement may also occur due to excessive wear, forces applied thereto during a revision surgery or other high load conditions.

SUMMARY OF THE INVENTION

Accordingly, there is a need for a stemless humeral component or prosthesis designed to preserve bone in initial implantation while enhancing initial pull-out resistance. Preferably enhanced initial dislodgement resistance will also provide excellent long term fixation. Furthermore, there is a need for new systems, kits and methods that minimize risk of dislodgement in a number of situations, including during revision, e.g., from an anatomical configuration to a reverse configuration or from a reverse to an anatomical configuration In one embodiment, a humeral anchor assembly is provided that includes a humeral anchor and at least one screw. The humeral anchor is configured to form a part of or support a part of a shoulder prosthesis. The humeral anchor has a distal portion configured to be anchored in a proximal region of a humerus and a proximal portion. The proximal portion includes a proximal face configured to engage an articular component within a periphery thereof. The proximal portion also includes at least one aperture disposed adjacent to the periphery. The at least one screw is disposed through the at least one aperture. The screw has a first end portion engaged with the proximal portion of the anchor and a second end portion disposed in or through cortical bone of the humerus.

In another embodiment, a humeral anchor kit is provided that includes a humeral anchor and at least one screw. The humeral anchor is configured to form a part of or support a part of a shoulder prosthesis. The humeral anchor has a distal portion configured to be anchored in a proximal region of a humerus and a proximal portion. The proximal portion includes a proximal face configured to engage an articular component within a periphery thereof. The proximal portion also includes at least one aperture disposed adjacent to the periphery. The aperture is configured to receive a screw advanced therethrough into bone disposed around or distal to the humeral anchor when implanted. The engagement of the humeral anchor having received the screw is enhanced.

In another embodiment, a method is provided for repairing a fracture of a humerus. The humerus has a superior portion superior to the fracture and an inferior portion inferior to the fracture. In the method a stemless humeral anchor is placed. The stemless humeral anchor has a proximal plate at a face of the superior portion of the humerus. The stemless humeral anchor has an aperture providing access from a proximal side to a distal side thereof. A screw is advanced through the aperture into the superior portion of the humerus. The screw is advanced through the fracture (f) into the inferior portion of the humerus.

In another embodiment, a surgical method is provided. In the method, a prosthetic shoulder joint comprising an anatomical configuration or a reverse configuration is exposed. A first articular component is removed. The first articular component has a convex surface corresponding to an anatomic configuration or a concave surface corresponding to a reverse configuration. A stemless humeral anchor is exposed by removing the articular component. A first screw is advanced through a first aperture of a plurality of peripheral apertures disposed about the stemless humeral anchor. The first screw is advanced into bone of the humerus. A second screw is advanced through a second aperture of the stemless humeral anchor and into cancellous bone of the humerus to enhance security of the stemless humeral anchor in the humerus. A second articular component is coupled to the stemless humeral anchor after the first screw and the second screw are advanced into the bone through the stemless humeral anchor.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of each of the drawings.

FIGS. 11(A)-11(C) illustrate a method of using the suture anchor assembly of FIG. 10 to provide a fracture repair;

DETAILED DESCRIPTION OF THE PREFERRED EMBODIMENT

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

Figure 1:
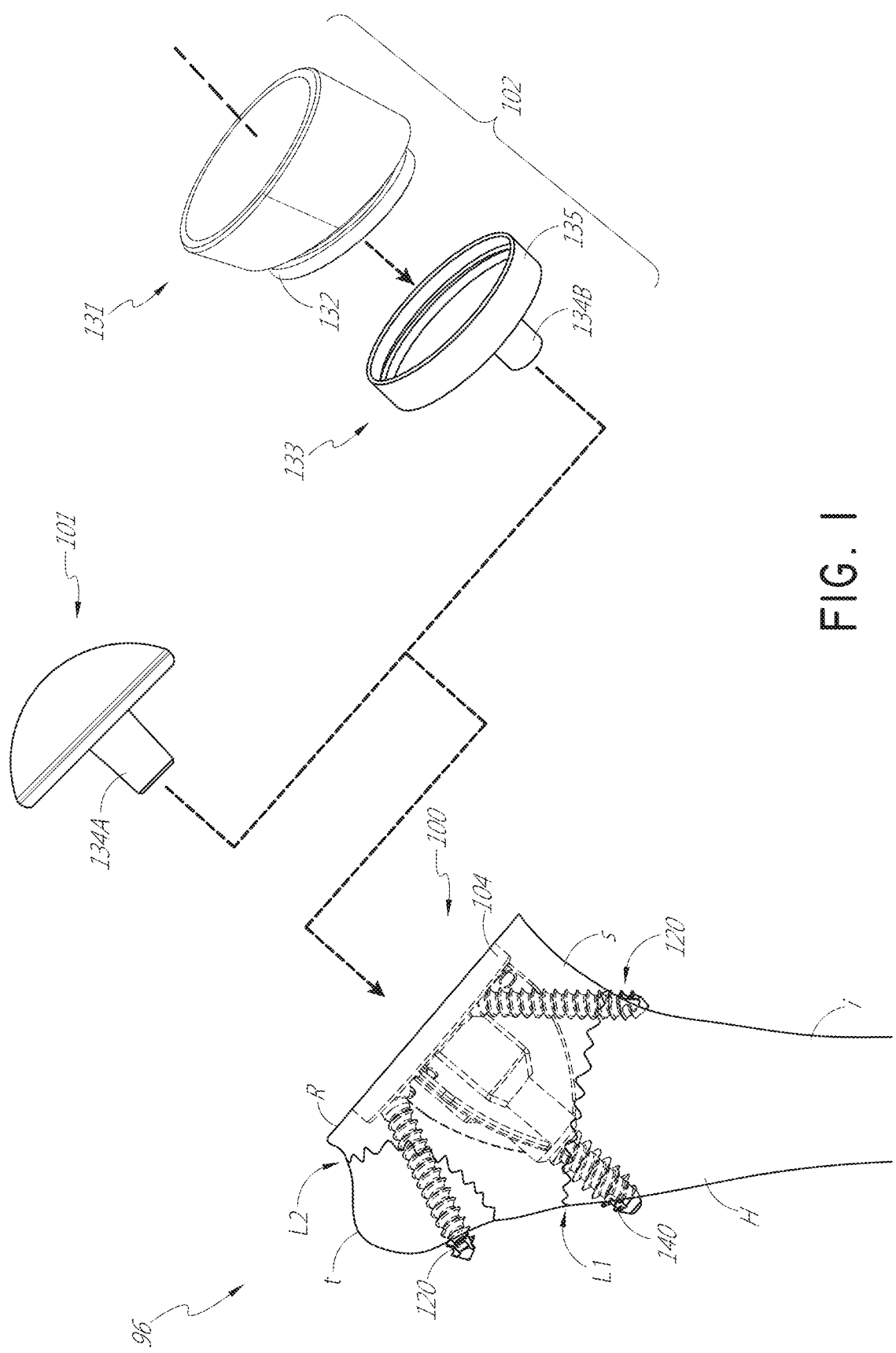
FIG. 1 shows a humeral anchor assembly configured to couple with an anatomic articular component and/or a reverse articular assembly and illustrates a kit for a surgical intervention or a revision procedure.

FIG. 1 shows a humeral assembly 96 that includes a humeral anchor assembly 100 having a humeral anchor 104. The humeral anchor 104 can be a stemless humeral anchor, as discussed further below. FIG. 1 shows two versions of the humeral assembly 96. In the first version of the humeral assembly 96, an articular component 101 of an anatomic prosthesis is mated with the humeral anchor 104. In a second version of the humeral assembly 96, the humeral anchor 104 is mated with an articular component 102 of a reverse prosthesis. For certain patients, a revision procedure can result in removing the anatomic articular component 101 and thereafter mating the reverse articular component 102 with the humeral anchor 104. It is also possible that for a patient the reverse articular component 102 could be removed and replaced with the anatomic articular component 101. These revision procedures would benefit from allowing the humeral anchor 104 to be left in place, but to be reinforced by one or more screws, forming the humeral anchor assembly 100 as discussed further below. The humeral anchor assembly 100 can provide a benefit in repairing one or more fractures L1, L2 of the humerus H in certain patients, either as part of a revision or in an initial humeral procedure. Certain embodiments herein include soft tissue or bone fragment anchoring features and methods of using such features to the benefit of patient. As discussed in further detail elsewhere herein, this application is directed to systems, kits and methods involving these features and functions.

Reinforcing Stemless Humeral Anchor

FIGS. 1-4 show an embodiment of the humeral anchor assembly 100 in which the humeral anchor 104 is coupled with one or more screws 120. The humeral anchor 104 preserves bone in initial implantation without requiring access to or modification of a medullary canal. The one or more screws 120 can enhance initial pull-out and dislodgement resistance, providing strong long term fixation. The screws 120 can be used in a revision procedure to enhance pull-out and dislodgement resistance subsequent to an initial procedure.

Figure 2:
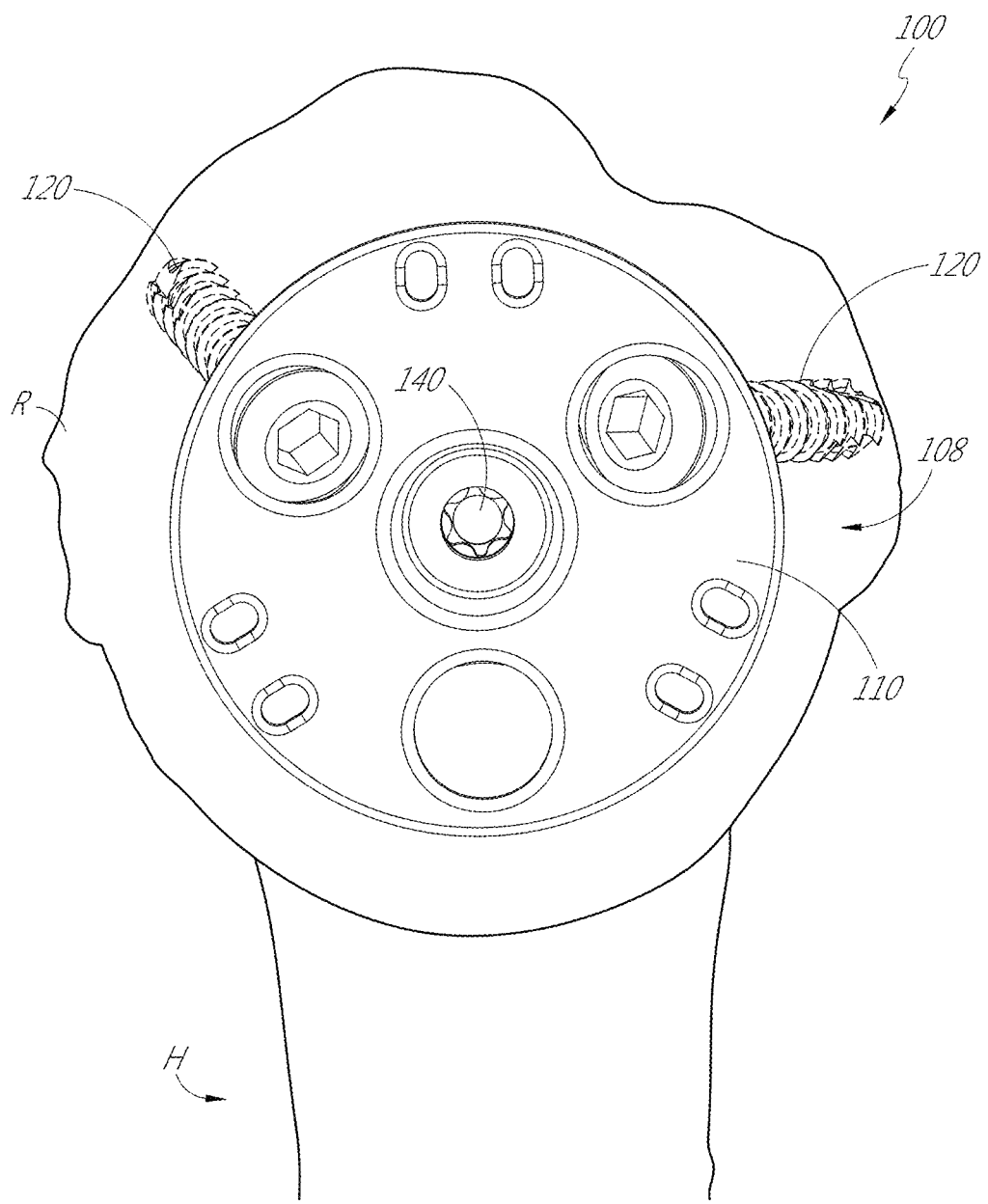
FIG. 2 shows a medial side of a humerus with the humeral anchor assembly of FIG. 1 implanted therein.
Figure 3:
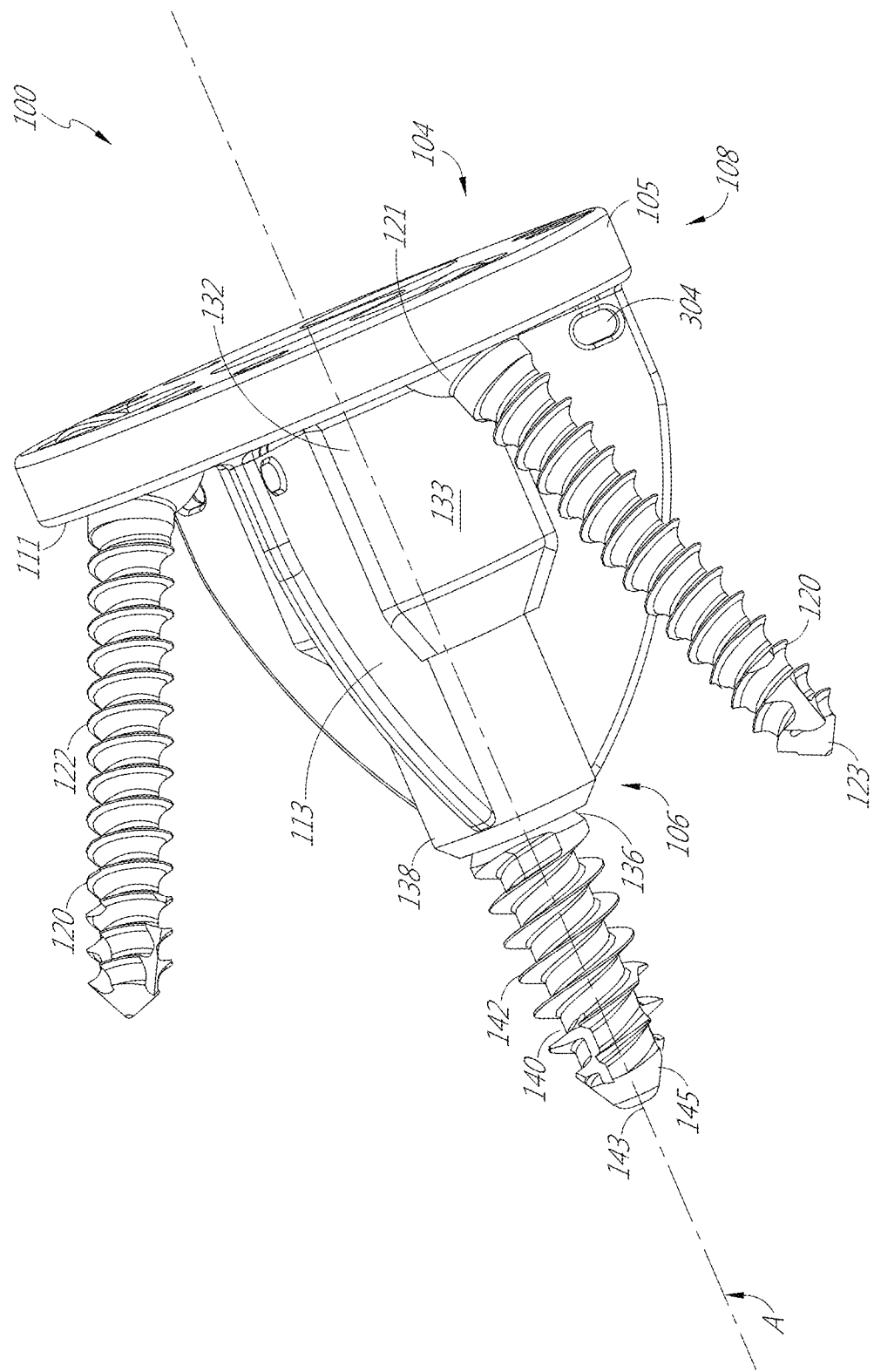
FIG. 3 is a side perspective view of the humeral anchor assembly of FIG. 1.

As shown in FIGS. 2-3, the humeral anchor 104 has a proximal portion 108 and a distal portion 106. The distal portion 106 has a tapered side profile with a greater outer profile or width dimension at a position closer to the proximal portion 108 of the humeral anchor 104 and a lesser profile or width dimension at a position farther away from the proximal portion 108. The tapered configuration of the distal portion 106 facilitates impaction of the distal portion 106 into a proximal region of a humerus H in a shoulder procedure. FIG. 2 shows the humeral anchor 104 of FIG. 1 implanted in the proximal humerus H. Prior to implantation of the humeral anchor 104, a portion of the humeral head including an articulating surface is resected, exposing a resection face R. The distal portion 106 of the humeral anchor 104 is driven into the humerus H such that a distal face 111 of the proximal portion 108 contacts the face R. In some techniques, the face R can be countersunk allowing the distal face 111 to be seated below the portion of the face R that is not countersunk. In one embodiment shown in FIGS. 1-4, the distal portion 106 comprises a plurality of, such as three, arms 113 extending between a distal end 138 of the distal portion 106 and the proximal portion 108. The arms 113 form the greater outer profile or width dimension of the distal portion 106 at the portion closer to the proximal portion 108 of the humeral anchor 104. The outer edges of the arms 113 can taper inwardly to form the lesser profile or width dimension of the distal portion 106 at the portion farther away from the proximal portion 108. The arms 113 advantageously enhance the contact surface between the distal portion 106 and the humerus H, preventing rotation of the humeral anchor 104 and allowing for more bony ingrowth without significantly increasing the impaction force required to drive the distal portion 106 into the proximal portion of the humerus H.

Figure 16:
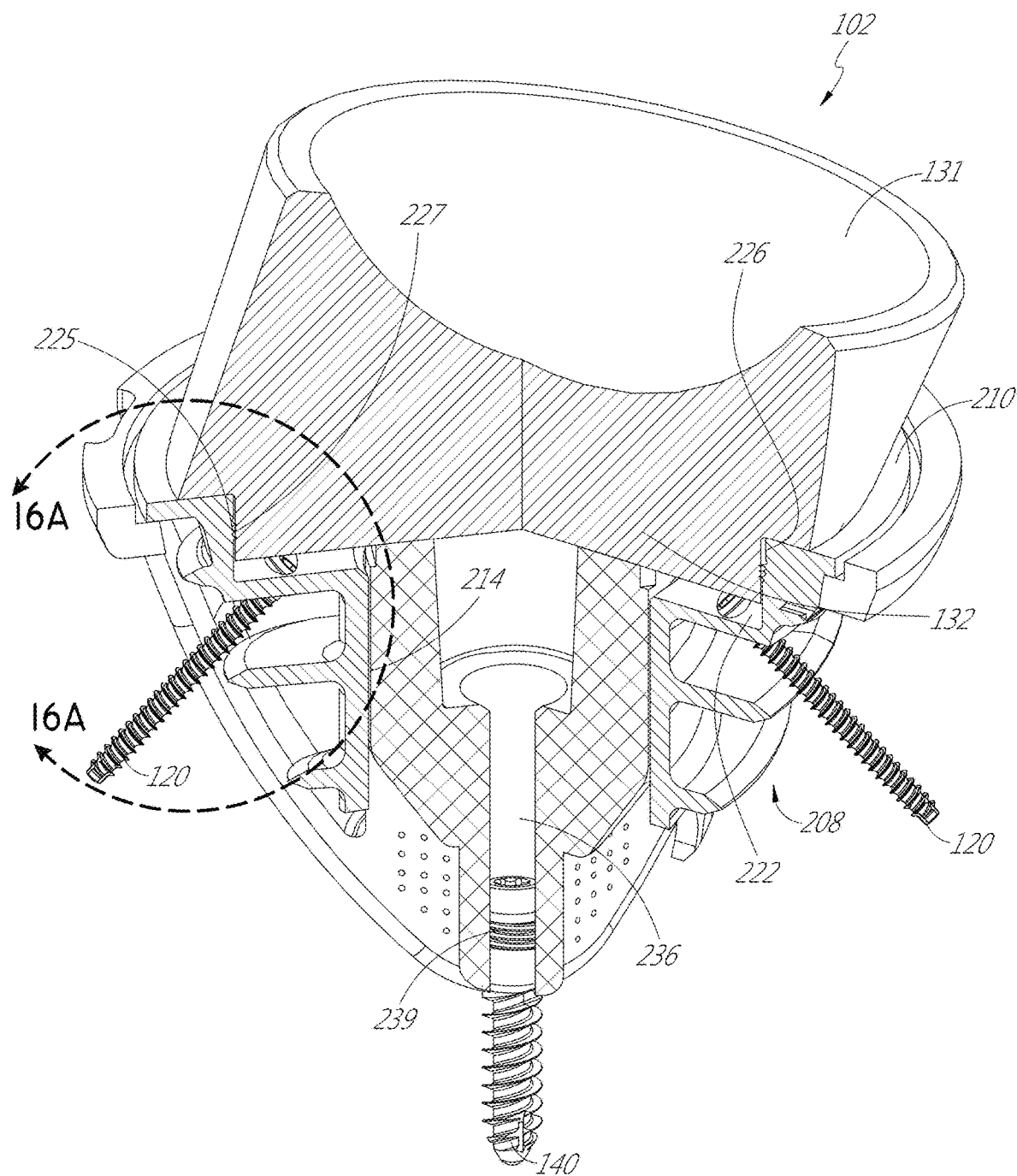
FIGS. 16 and 16A show a cross-sectional view of the connection of an articular component or assembly to the humeral anchor of FIG. 12 or humeral anchor assembly of FIG. 13.
Figure 16A:
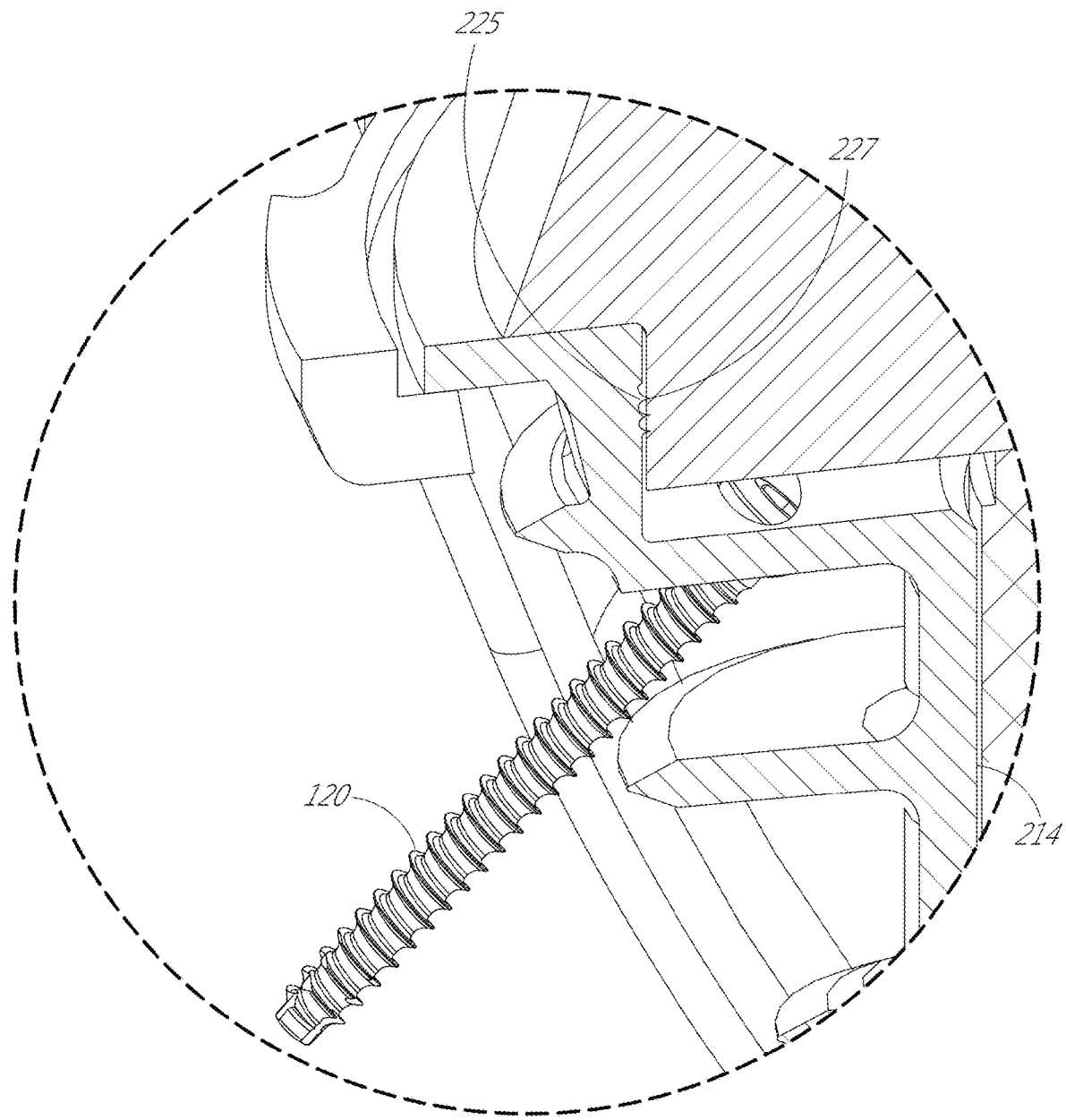

In the embodiment shown in FIGS. 1-4, the proximal portion 108 is integrally formed with the distal portion 106 such that the proximal portion 108 and the distal portion 106 can be placed in the humerus H simultaneously. The proximal portion 108 also has a proximal face 110 facing away from the face R when the anchor 104 is implanted. The proximal face 110 is generally flat, e.g., substantially planar, and has a periphery 112. The proximal face 110 also has a mating structure configured to securely engage the anatomical articular component 101 in one combination. For example, a projection 134A of the anatomical articular component 101 can be received in a recess of the proximal face 110 in one combination. In another combination, the proximal face 110 can be configured to engage the reverse articular component 102 by mating with a projection 134B of a mating portion 133 that provides an interface between the humeral anchor 104 and an articular portion 131 of the reverse articular component 102. In another combination, the humeral anchor 104 directly engages the articular portion 131. FIG. 1 shows the reverse articular component 102 includes both the articular portion 131 and the mating portion 133. The mating portion 133 includes the projection 134B on a distal end and a raised portion 135 on a proximal end thereof. The raised portion couples with the articular portion 131. The coupling or connection between the articular portion 131 and the raised portion 135 can take any suitable form. For example, a spring member, a bayonet connection, or other interlocking feature can be provided to secure together these components of the articular component 102. FIGS. 16-16A show in the context of another embodiment described below that an interference fit can be used to couple the articular component 131 to the another structure. In the embodiment of FIGS. 1-3 an interference fit connection can be provided between the articular component 131 and the mating portion 133. The mating of the proximal face 110 with the projection 134A or the projection 134B may be secured mechanically, such as by a Morse taper, by a press fit, or with adhesives, or other methods that would be apparent to one of ordinary skill in the art. In one embodiment of the present disclosure shown in FIG. 2A, the mating structure is a concave structure 132 projecting distally from the proximal face 110.

Figure 2A:
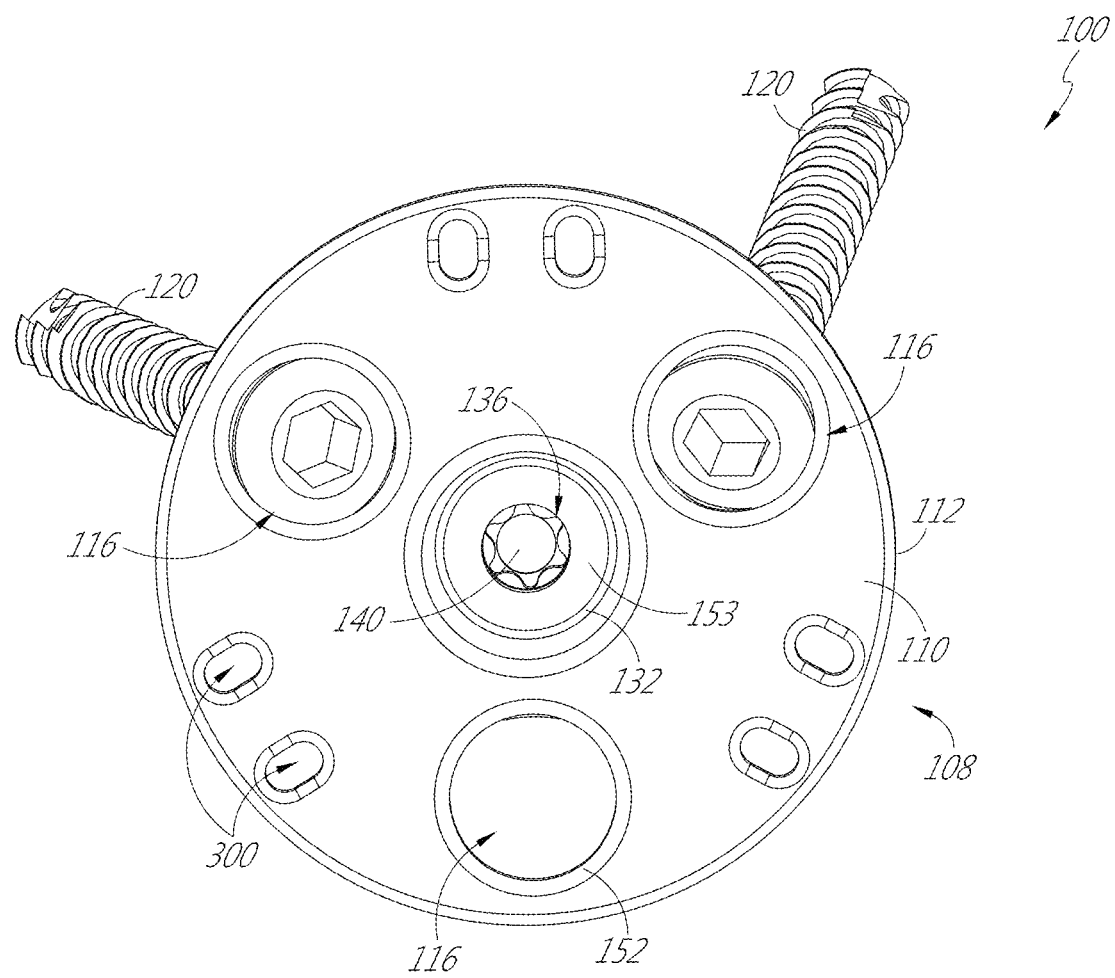
FIG. 2A shows a medial side of the humeral anchor assembly of FIG. 1.

FIG. 2A shows that the proximal portion 108 can include at least one aperture 116 disposed adjacent to the periphery 112. In the embodiment shown in FIGS. 1-4, the proximal portion 108 includes a plurality of, e.g., three, apertures 116 adjacent to the periphery 112. The centers of the apertures 116 can be surrounded by, e.g., from a circle that is concentric to, the periphery 112. The apertures 116 can be substantially evenly spaced, that is, about 120° apart. An evenly spaced configuration permits the humeral anchor 104 to be applied to the face R in any rotational orientation. In other embodiments, a preferred orientation can provide non-uniform spacing between the apertures 116, e.g., with two of the apertures positioned closer to each other and a third aperture spaced farther apart from the two closely positioned apertures. The proximal face 110 may have other number of and/or configuration of the apertures 116.

In the embodiment shown in FIGS. 1-4, the proximal portion 108 can also include an opening 136 that is disposed away from the periphery 112, e.g., that is substantially concentric to the periphery 112. The opening 136 can open into a lumen that extends through a segment of the distal portion 106 of the humeral anchor 104. The opening 136 can be accessed along a path extending from the proximal portion 108 through the distal portion 106. In one embodiment, the opening 136 is accessed through and can also be substantially coaxial with the concave structure 132. The opening 136 can be located on a distal end 133 of the concave structure 132 to provide access through the lumen (if present) or directly to bone matter disposed distally of the humeral anchor 104. Advantages of having a plurality of apertures in the configuration as shown in this embodiment, e.g., disposed adjacent to and spaced away from the periphery 112, are disclosed in more detail below.

Figure 4:
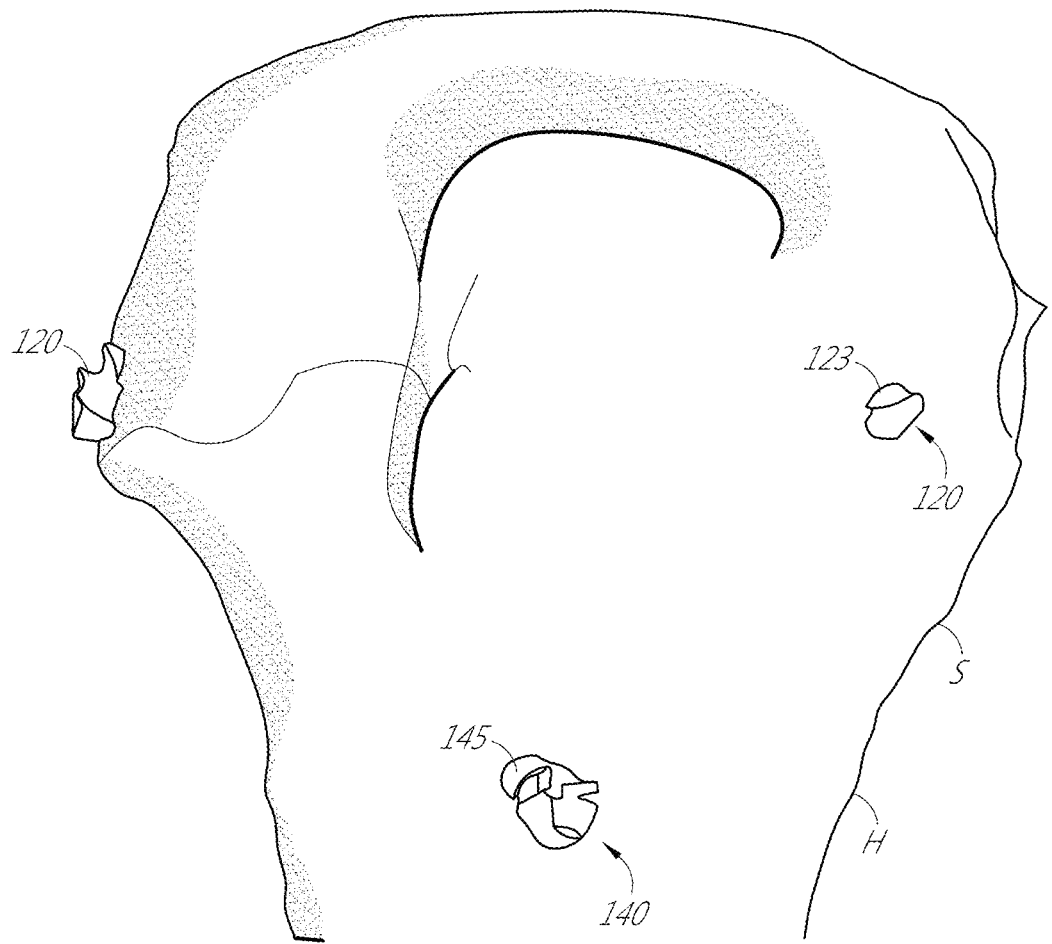
FIG. 4 is a view of the lateral side of the humerus, showing the position of distal ends of three screws of the humeral anchor assembly of FIG. 1.

As further shown in FIGS. 1-2 and 4, in one method and in one humeral anchor assembly 100 two screws 120 are disposed through two of the apertures 116 and into the bone of the humerus H. The screws 120 reinforce the connection between the humeral anchor 104 and the humerus H. The screw 120 can include an approximately spherical head 121 on a proximal end thereof, a threaded portion 122 on a distal end, and a blunt atraumatic tip 123. The threaded portion 122 has an outer diameter that is smaller than a diameter of the aperture 116 so that the threaded portion 122 can be inserted into the humerus H through the aperture 116, allowing the threaded portion 122 to extend to and through cortical bones of the humerus H. A difference between diameter of the threaded portion 122 and the diameter of the aperture 116 can be sufficient to allow the screw 120 to move to a selected angular position relative to the proximal portion 108 as appropriate for a specific patient or procedure. The spherical head 121 has a diameter that is larger than the diameter of the aperture 116 such that the approximately spherical head 121 acts on a portion of the humeral anchor 104 around the aperture 116 to press the distal face 111 against the face R or into a counter-sunk region of the humerus H. This action enables the screw 120 to enhance engagement of the humeral anchor 104 with the humerus H. The screw 120 can be a self-tapping compression screw or any other types of screw known in the art.

As shown in FIG. 4, after the screw 120 has been implanted in the humerus H, an unthreaded portion 123 may extend outside a surface S of the humerus H. The threaded portion 122 preferably extends into but not fully through the cortical bones of the humerus H. A distal-most end of the threaded portion 122 is disposed beneath the surface S of the humerus H as the screw 120 penetrates the surface S. Retaining the distal-most end of the threaded portion 122 beneath the surface S advantageously reduces or eliminates interaction between the threaded portion 122 and the soft tissue disposed around the humerus H adjacent to the surface S. The unthreaded portion 123 extending outside the surface S of the humerus H may advantageously allow visual confirmation by a surgeon that the screw 120 has been implanted in an intended location and advanced sufficiently far to provide good support for the humeral anchor 104.

FIGS. 1-4 show that in some embodiments of methods and of the humeral anchor assembly 100, a central screw 140 may be disposed distally of the opening 136, e.g., in a lumen disposed between the opening 136 and the distal end 138 of the humeral anchor 104. The central screw 140 may have the same shape and dimension as the screw 120, or it may have a different shape or dimension than the screw 120. In one embodiment as shown in FIGS. 1-4, the central screw 140 has a threaded portion 142 that is larger and longer than the threaded portion 122 of the screw 120. A distal portion 145 of the central screw 140 between the threaded portion 142 and a distal end 143 of the screw 140 may be tapered to dilate the cancellous bone through which the central screw 140 may be place.

A plurality of apertures 116 in the configurations shown in FIGS. 1-4 provide the ability to select the degree of additional pull-out resistance or reinforcement to be provided. For example, in one method a central screw 140 is provided and is sufficient to provide additional securement of the humeral anchor 104, e.g., in a revision procedure. In another method, one peripheral screw 120 is provided and is sufficient to provide additional securement of the humeral anchor 104, e.g., in a revision procedure. In other methods, more than one screw 120, 140 is provided. For example, one peripheral screw 120 and one central screw 140 can be provided to provide additional securement of the humeral anchor 104, e.g., in a revision procedure. In other methods two peripheral screws 120 can be provided to provide additional securement of the humeral anchor 104 in a revision or other procedure. In other methods three peripheral screws 120 can be provided to provide additional securement of the humeral anchor 104 in a revision or other procedure. In other methods three peripheral screws 120 and a central screw 140 can be provided to provide additional securement of the humeral anchor 104 in a revision or other procedure. Providing a plurality of screw 120, 140 through the apertures 116 and the opening 136 or a lumen disposed distal of the opening 136 yields greater pull-out resistance than having a single screw. Having spaced apart screws 120, 140, e.g., uniformly spaced apart screws 120, advantageously allow dispersion, e.g., substantially uniform distribution, of load on the screws 120, 140. These approaches provide greater reinforcement of the humeral anchor 104 in the humerus H.

In the embodiment shown in FIGS. 1-4, there is a concave, spherical surface 152 (or other curved surface) disposed between each aperture 116 and the proximal face 110. A curved surface 153 can be disposed between the opening 136 and the space defined within the concave structure 132. The spherical head 164 of the screw 120 can rotatably mate with the concave, spherical surface 152 such that the screws 120 can be implanted into the humerus H at a selected angle, e.g., at an angle and projects radially outward and away from a longitudinal axis A of the humeral anchor 104. An embodiment providing angulation of the screws 120 advantageously provides greater pull-out resistance than a configuration in which the screws 120 are implanted parallel to the longitudinal axis A of the humeral anchor 104. An embodiment providing angulation of the screws 120 advantageously allows the screws 120 to reach and to engage the cortical bone of the humerus H, which is located on the outer surface of the humerus H. For example, the shortest trajectory to cortical bone may be at an angle other than perpendicular to the proximal face 110, as shown in FIGS. 2A and 3. The ability to angulate the screws 120 allows the surgeon to reach the cortical bone with a shorter screw and/or with less traumatic bone interaction.

Figure 17:
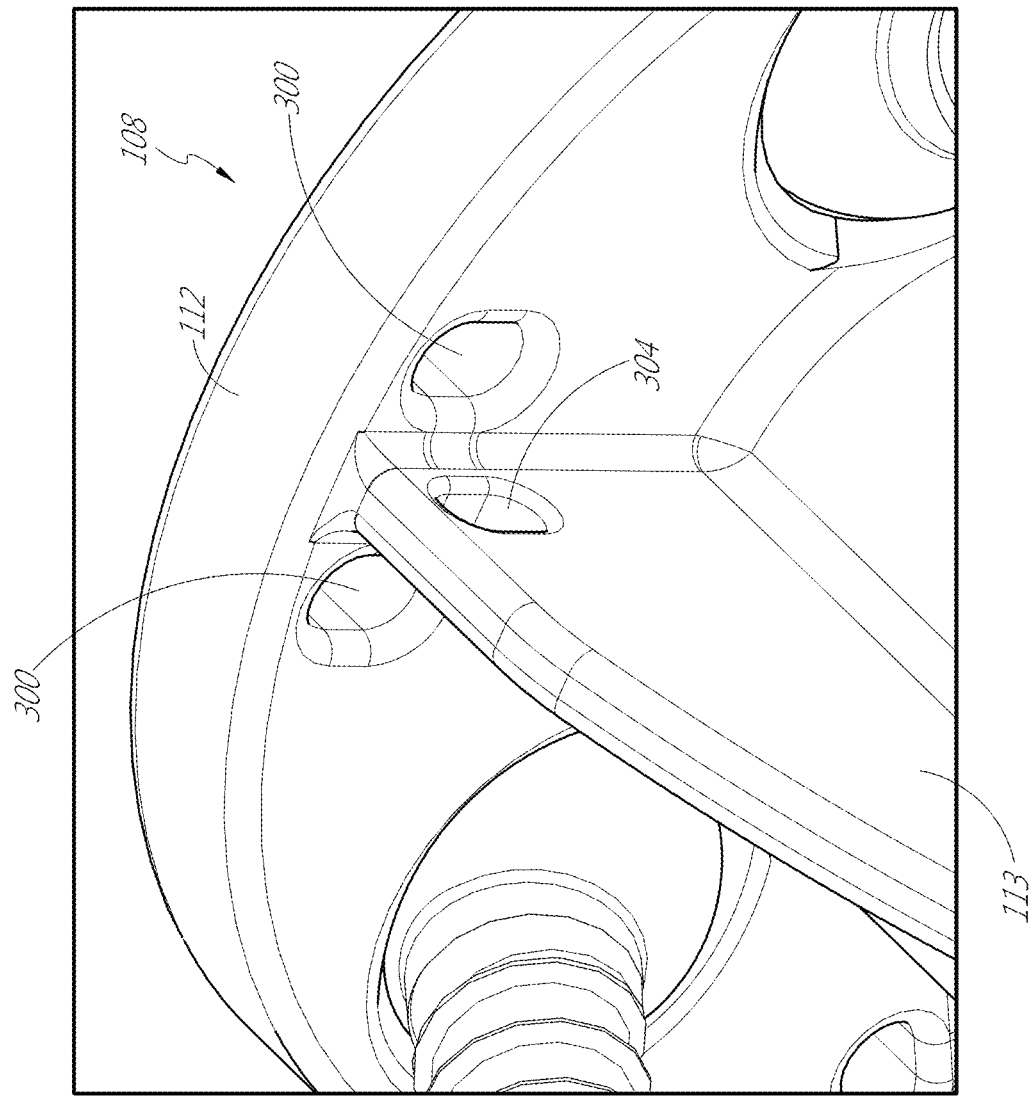
FIG. 17 shows an embodiment of a humeral anchor including anchor features for securing a suture in connection with a procedure involving the humeral anchor.

FIGS. 2A and 3 show that in various embodiments, the humeral anchor 104 can have at least one anchor feature 300, 304 disposed adjacent the outer periphery 112. The anchor feature 300 is located on the proximal portion 108 adjacent the outer periphery 112. The anchor feature 304 is located on one of (or on each of) the arms 113 at a location adjacent the outer periphery 112. The anchor features 300, 304 are shown in more detail in FIG. 17 and can be configured to secure a suture, as described in more detail below.

FIGS. 12-15 show another embodiment of a humeral anchor assembly 200 having a two-piece stemless humeral anchor 204. The humeral anchor 204 is similar to the humeral anchor 104 except as described differently below. Features of the humeral anchor 204 that are not mutually exclusive of the humeral anchor 104 can be incorporated into the humeral anchor 104. Features of the humeral anchor 104 that are not mutually exclusive of the humeral anchor 204 can be incorporated into the humeral anchor 204. The humeral anchor assembly 200 can be reinforced by one or more screws 120, 140 in a manner similar to that described herein in connection with the humeral anchor assembly 100.

The two-piece stemless humeral anchor 204 is configured to retain the anatomical articular component 101, the reverse articular component 102, or the articulating portion 131 directly (as discussed further below) without requiring access to or modification of a medullary canal.

Figure 15:
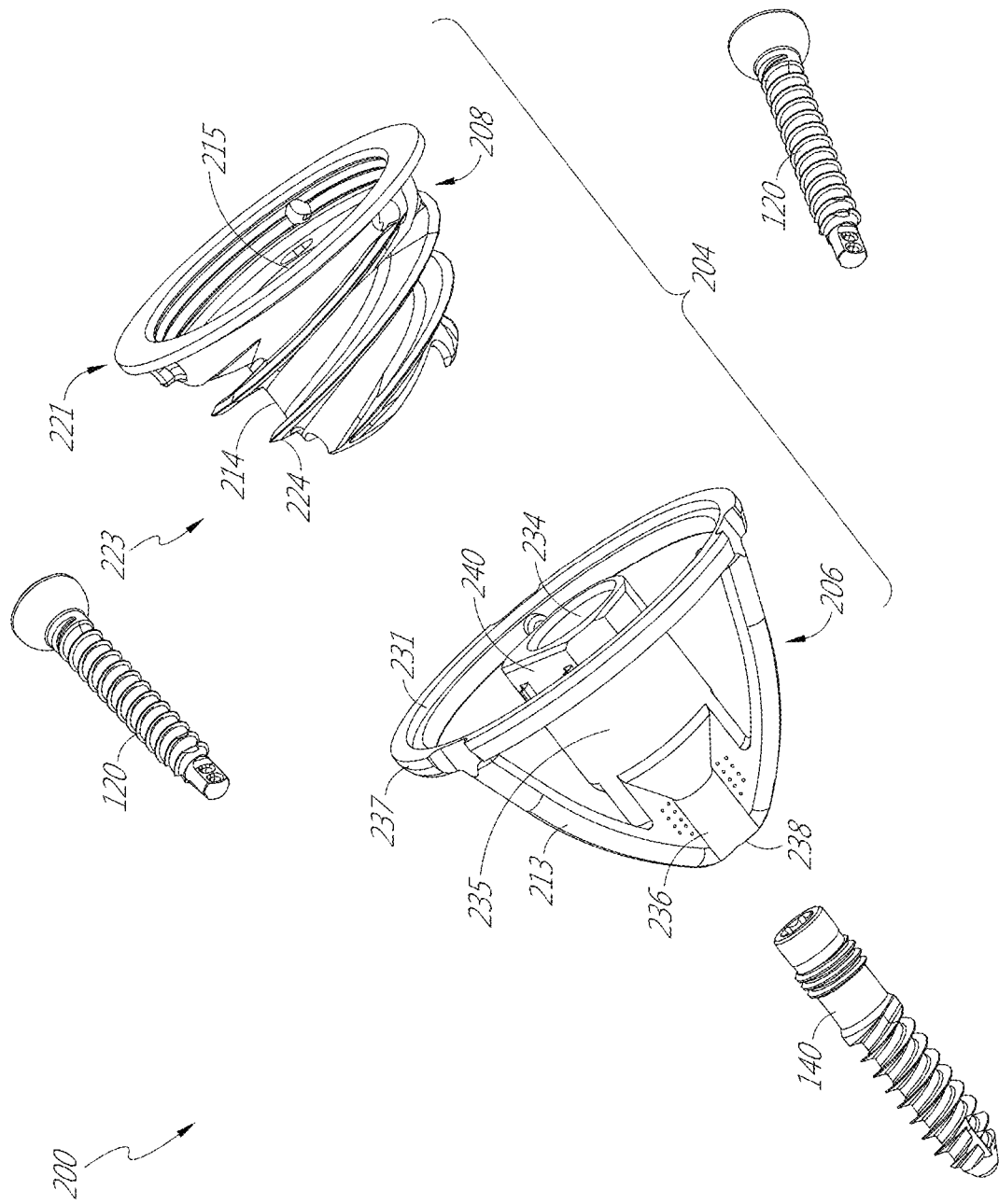
FIG. 15 is an exploded view of a humeral anchor assembly of FIG. 13.

As shown in FIG. 15, the two-piece stemless humeral anchor 204 has a proximal portion 208 and a distal portion of 206 that are separable from each other such that the proximal portion 208 and the distal portion 206 can be placed in the humerus H separately. That is, the distal portion 206 can be placed in the humerus H first and the proximal portion 208 can be placed into the distal portion 206 and into the humerus thereafter. The distal portion 206 has a distal end 238 configured to be embedded in bone and a proximal end which includes a ring 237 configured to be disposed at or close to the face R of the humerus H. The distal portion 206 also has a plurality of spaced apart arms 213 extending between the distal end 238 and the ring 237.

The distal portion 206 includes a concave structure 234 comprising an opening configured to receive the projection 134A of the anatomical articular component 101 or the projection 134B of the reverse articular component 102. In the illustrated embodiment, the proximal portion 208 is configured to retain the articular portion 131 directly, as discussed below. In one embodiment, the concave member 234 comprises a body coupled with the arms 213 at or adjacent to the distal end 238 of the distal portion 206. A continuous expanse of material can be provided between the arms 213 and the body of the concave member 234. The body and the arms 213 can be provided as a monolithic structure. The body can be a cantilever extension from the distal end 238 of the distal portion 206. A proximal end of the body of the concave member 234 can comprise an opening configured to mate with the projection 134A or the projection 134B. The proximal end of the proximal portion 208 can include features of the raised portion 135 of the mating portion 133 shown in FIG. 1. A distal end of the concave member 234 can include an aperture 236. The aperture 236 can be similar to the aperture 136 of the humeral anchor 104, e.g., configured to receive the screw 140 and/or to provide access to a lumen within which the screw 140 can be disposed. In one embodiment, the distal portion 206 and/or the proximal portion 208 also comprise at least one of the anchor features 300 or 304 as discussed in connection with the humeral anchor 104

Figure 13:
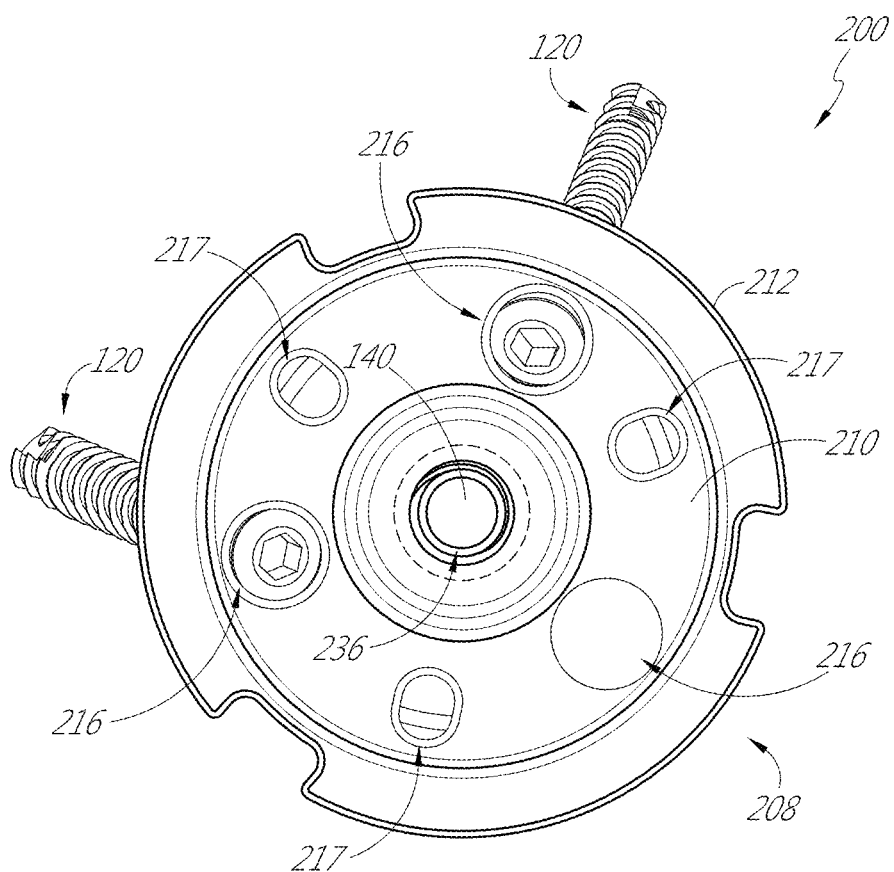
FIG. 13 shows a medial side of a humeral anchor assembly including a plurality of screws and the humeral anchor of FIG. 12.
Figure 14:
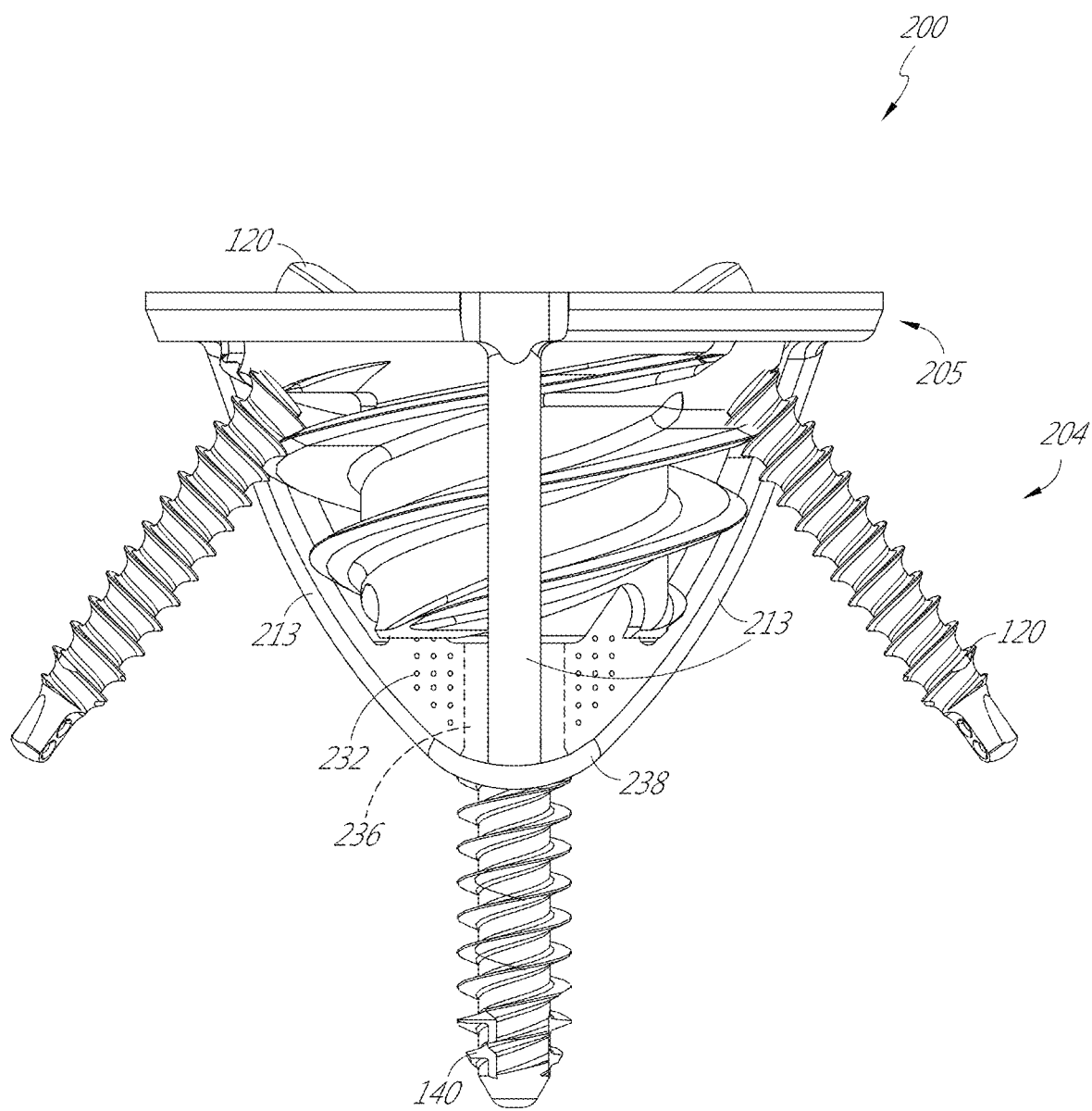
FIG. 14 is a side view of the humeral anchor assembly of FIG. 13.

The proximal portion 208 has a proximal face 210 adapted to be disposed at or adjacent to the ring 237 when the proximal portion 208 is advanced into the distal portion 206 and when both are placed in the humerus H to be disposed at or adjacent to the face R. As shown in FIG. 13, the proximal face 210 may include one or more apertures 216 that are similar to the apertures 116 of the humeral anchor 104. The apertures 216 are configured for engaging the screw 120 in a manner similar to the apertures 116. The proximal portion 208 has a proximal end 221 and a distal end 223. The distal end 223 is advanceable into the distal portion 206. The distal end 223 is advanceable into the humerus H. The proximal face 210 can include one or more tooling features 217. The tooling features 217 can be disposed between the apertures 216, e.g., spaced apart by substantially equal amounts. Non-uniform spacing can be provided between the tooling features 217 in some embodiments. In some embodiments, the tooling features 217 can include one, two, three, four or more tooling features. The tooling features can aid in coupling the proximal portion 208 to a tool for advancing the proximal portion 208 into the distal portion 206 and into the humerus H. The tooling features 217 can take many suitable forms. In the illustrated embodiment, the tooling features 217 are three spaced apart recesses that are formed on the proximal face 210. The recesses can be simultaneously engaged by a tool and can each bear about one-third of the torque applied to the proximal portion 208 to advance it into the distal portion 206 and into the humerus H. When so advanced, the proximal portion 208 extends into the cancellous bone disposed peripherally of the distal portion 206 to enhance retention of the humeral anchor 204. The proximal portion 208 also includes a cylindrical sleeve 214. An inner periphery of the sleeve 214 can be selected to allow the proximal portion 208 to be advanced over the body of the concave member 234. Relative sizes of an outer periphery 235 of the body of the concave member 234 and the sleeve 214 can be selected such that there is no resistance to advancement of the sleeve 214 relative to the body but such that a close fit is provided, e.g., a slip fit. FIG. 15 shows that in one embodiment, the outer periphery 235 of the body of the concave member 234 includes an anti-rotation feature, such as a flat edge 240. The flat edge 240 or other anti-rotation feature helps prevent rotation of an articular component coupled with the humeral anchor 204. FIG. 15 shows that the ring 237 on the distal portion 206 can also have a shelf 231 on an inner portion of the ring 237. The shelf 231 receives a distal face of the proximal portion 208 providing a positive stop for advancement of the proximal portion 208 into the distal portion 206 and thereby into the humerus H when the distal face opposite the proximal face 210 contacts a surface of the ring 237. In one embodiment, the proximal portion 208 also has external threads 224 on the distal end 223 and the proximal portion 208 can be threaded into the humerus H. Threaded mating of the proximal portion 208 and the humerus H advantageously provides additional pull-out resistance.

Turning to FIGS. 16 and 16A, an embodiment for direct mating of the proximal portion 208 and the articular portion 131 is shown. In this embodiment, the proximal portion 208 includes a concave recess 222 that extends between an inner edge of the proximal face 210 and the inner periphery of the sleeve 214. The concave recess 222 can have ridges 225 disposed on an inner periphery sidewall 226 of the concave recess 222. The ridges 225 can be configured to capture a protrusion 132 of the articular portion 131 of the reverse articular component 102. For example, the inner periphery of the concave recess 222 defined by peaks of the ridges 225 can be smaller than an outer periphery or an outer dimension of the protrusion 132. An interference fit can therefore be provided between the protrusion 132 and the concave recess 222, e.g. the ridges 225, when the articular portion 131 is engaged with or coupled to the proximal portion 208. In particular, the outer periphery of the protrusion 132 of the articular portion 131 is larger than a dimension of the concave recess 222 defined transversely across the concave recess 222 between the peaks 227 (see FIG. 16A) of the ridges 225 on opposite sides of the concave recess 222. The peaks 227, where provided, can be pointed or rounded in different embodiments. The outer periphery of the protrusion 132 of the articular portion 131 is smaller than the dimension defined by the base of the ribs or ridge 225 or defined by the sidewall 226 from which the ribs or ridges 225 extend. As a result, the articular portion 131 can be inserted into the concave recess 222 but with some interference with the peaks 227 of the ridges 225 to provide an interference fit. In some embodiments, ridges 225 could alternatively or additionally be provided on the protrusion 132 of the articulating portion 131. In some embodiments, the protrusion 132 can include other members or features that provide an interference fit between the protrusion 132 and the concave recess 222 when the articulating portion 131 is engaged with or coupled to a humeral anchor. In other embodiments, a snap-fit connection can be provided between the articular portion 131 and the recess 222, e.g., using a C-ring disposed in a circumferential channel formed in the sidewall 226 and/or in the protrusion 132.

Preferably the ridges 225 extend entirely around the inner periphery sidewall 226 of the concave recess 222. The ridges 225 could extend along arcs including less than 180 degrees of the inner periphery sidewall 226. The ridges 225 could extend along arcs including less than 90 degrees of the inner periphery sidewall 226. The ridges 225 could extend along arcs including less than 45 degrees of the inner periphery sidewall 226. The ridges 225 could extend along arcs including less than 30 degrees of the inner periphery sidewall 226. The ridges 225 could extend along arcs including greater than 180 degrees of the inner periphery sidewall 226.

In another embodiment, a surgical method using the humeral anchor assembly 100 or 200 is provided. The surgical method comprises a revision procedure to be performed on a patient who has previously undergone a shoulder joint replacement surgery, during which a humeral anchor 104, 204 was implanted in the patient's humerus. The humeral anchor 104, 204 may or may not have been reinforced by one or more screws in the prior procedure. In the prior procedure the humeral anchor 104, 204 is mated with an articular component 101 of an anatomic prosthesis or an articular component 102 of an reverse prosthesis.

During the revision procedure, the previously implanted prosthetic shoulder joint comprising the anatomical configuration or the reverse configuration is exposed. The first articular component, such as the anatomic articular component 101 or the reverse articular component 102, is removed from the humeral anchor 104, 204. The first articular component has a convex surface corresponding to an anatomic configuration or a concave surface corresponding to a reverse configuration. In a previous surgery in which an articulating portion 131 of the reverse prosthesis was directly coupled to a proximal portion 208 of the humeral anchor 204, the articulating portion 131 is removed. Upon removing the first articular component, a stemless humeral anchor 104 or 204 is exposed.

A first screw 120 is advanced through a first aperture 116 or 216 of a plurality of peripheral apertures 116, 216 disposed about the humeral anchor 104 or 204. The first screw 120 is advanced into bone of the humerus H and preferably into the cortical bone of the humerus H opposite the face R. In one embodiment, the first screw 120 may also be advanced at an angle projecting away and outward from the longitudinal axis of the humeral anchor 104 or 204. In some embodiments, a second screw 120 is advanced through another aperture 116 or 216 of the plurality of peripheral apertures. In a previous surgery in which one or more of screws 120 were implanted, the previously implanted screws 120 may be removed if the previously implanted screws became loose during removal of the first articular component, and new screws may be implanted, for example with larger or a different configuration of threads. In another embodiment, the previously implanted but loosened screws may be tightened using a standard tightening tool, such as a torque-limiting screw driver, instead of being replaced by new screws. In another embodiment, an additional screw may be advanced through another peripheral aperture 116 or 216 that did not receive a screw in the previous surgery.

In one method, a second screw 140 is also advanced through the aperture 136 or the aperture 236 of the humeral anchor 104, 204 and into cancellous bone of the humerus to enhance security of the stemless humeral anchor 104 or 204 in the humerus H. In one embodiment, the second aperture 136, 236 is located centrally, along or adjacent to a longitudinal axis A of the stemless humeral anchor 104 or 204. In some embodiments, at least a portion of an inner wall of the aperture 236 of the humeral anchor 204 comprises threads 239. As shown in FIG. 16, the threaded portion 142 of the second screw 140 can mate with the threads 239 on the inner wall of the aperture 236 as the screw 140 is advanced through the aperture 236 and into the humerus. The mating between the threaded portion 142 of the second screw 140 and the threads 239 of the humeral anchor 204 can further enhance initial pull-out and dislodgement resistance, providing strong long term fixation.

After the first screw 120 and the second screw 140 are advanced into the bone through the humeral anchor 104, 204, a second articular component 101 or 102 can be coupled to the stemless humeral anchor 104 or 204. In some embodiments, the articular portion 131 of a reverse prosthesis is coupled directly to the stemless humeral anchor 104, 204 as described above. If the first articular component is adapted for an anatomical configuration, the second articular component can be adapted for a reverse configuration. If the first articular component is adapted for a reverse configuration, the second articular component can be adapted for an anatomical configuration. In some techniques, an anatomic articular component 101 can be replaced with another anatomic articular component 101. In some techniques, a reverse articular component 102 or a reverse articular portion 131 can be replaced with another reverse articular component 102 or reverse articular portion 131.

Fracture Repair Using Humeral Anchor Assemblies

Figure 10:
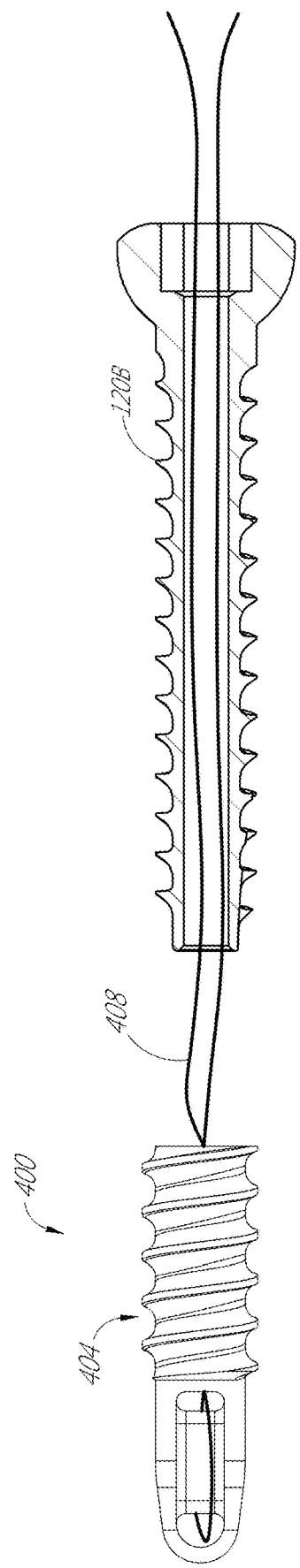
FIG. 10 is a suture anchor assembly that can be coupled with a humeral anchor and that is configured to facilitate fracture repair and/or soft tissue anchoring.
Figure 11C:
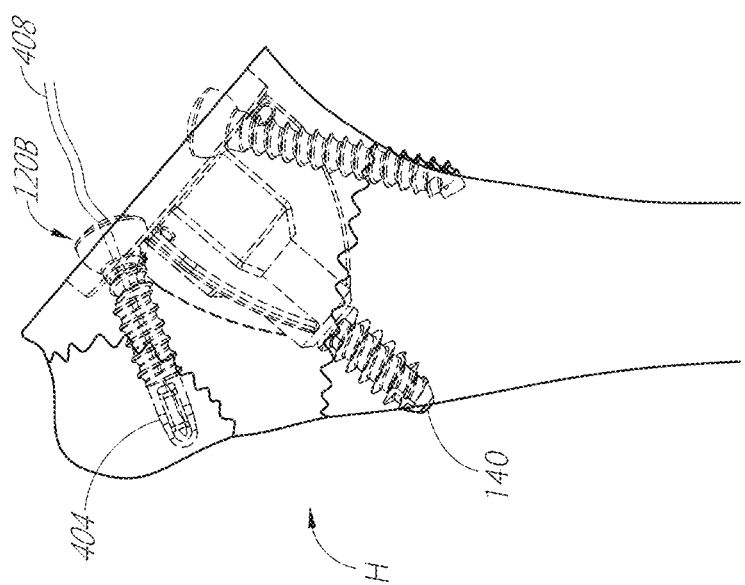
Figure 12:
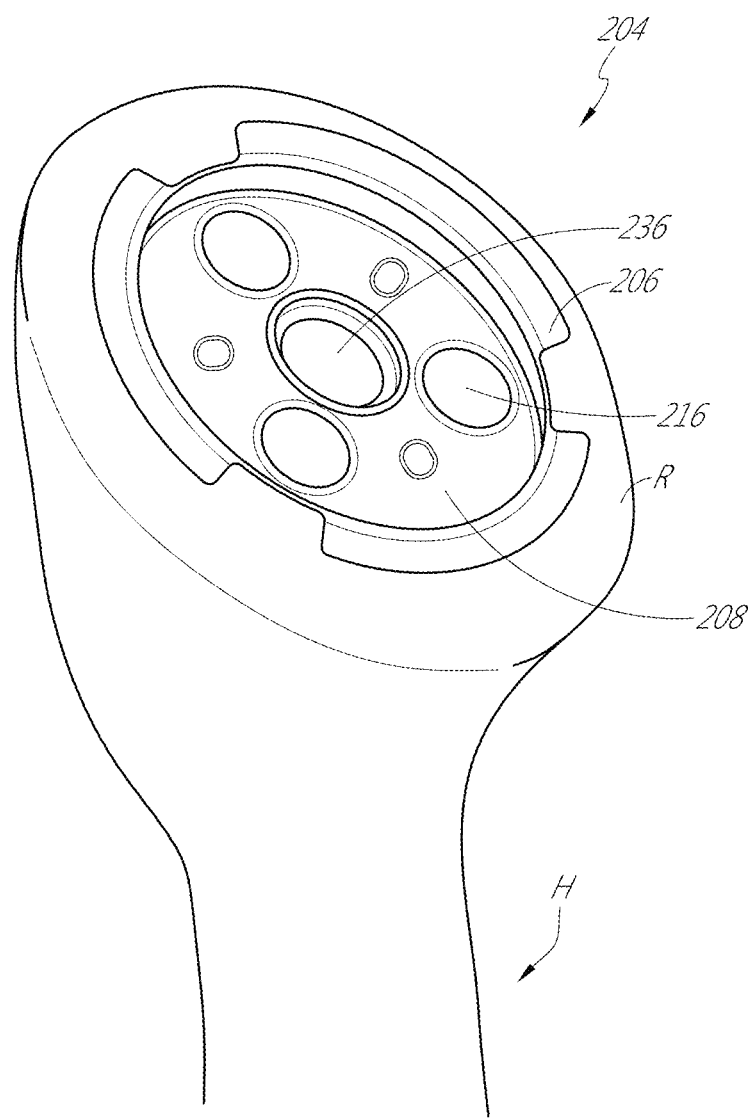
FIG. 12 shows another embodiment of a humeral anchor configured to retain an articular component without requiring access to or modification of a medullary canal.

FIGS. 10-11C show a method for repairing a fracture of a humerus H using a humeral anchor assembly 100 or 200. The humerus H has a superior portion "s" superior to the fracture and an inferior portion "i" inferior to the fracture. For example, in the illustrated embodiment the fracture may be a fracture L1 at a neck of the humerus. The neck of the humerus may be located at a constriction below tubercles of the humerus. The superior portion s and the inferior portion i are separated at a neck fracture L1. The inferior portion i of the humerus can include a diaphysis of the humerus H.

In this method, the face R of the superior portion s of the humerus is prepared by resecting part of the superior portion s of the humerus, as discussed above. A stemless humeral anchor 104 or 204 is implanted into the superior portion s of the humerus. For example, the bone beneath the face R can be prepared by a tool that creates space in cancelleous bone shaped to receive the arms 113, 213 and other portions of the anchors 104, 204 to be disposed beneath the face R. The stemless humeral anchor 104 is implanted as one unitary component. The stemless humeral anchor 204 is placed in the humerus by first implanting the distal portion 206 into the humerus H. Thereafter, the proximal portion 208 is advanced into the distal portion 206 and into the humerus H, e.g., by being threaded into the humerus H.

After the stemless humeral anchor 104 or 204 has been implanted, a proximal plate 105 or 205 of the stemless humeral anchor 104 or 204 is disposed at or recessed into a countersunk region at the face R of the superior portion s of the humerus. The plate 205 can comprises the combination of the ring 237 and the proximal end 221 of the proximal portion 208. The stemless humeral anchor 104 or the proximal portion 208 of the humeral anchor 204 has one or more apertures or openings 116, 136, 216, and 236 providing access from a proximal side of the stemless humeral anchor 104 or 204 to a distal side thereof. One or more screw 120 and 140 can be advanced through the apertures or openings 116, 136, 216, or 236 into the superior portion s of the humerus. The screws 120 and 140 are also advanced past the fracture L1, L2 into the inferior portion i of the humerus such that the screws 120 and 140 span across the fracture L1, L2. The screws 120 not only provide fixation of the superior portion s to the inferior portion i of the humerus, but also promotes healing of the fracture L1 by pulling the superior portion s and the inferior portion i tightly against each other and thereby stimulating bone growth at the fracture L1.

In some embodiments, the proximal plate 105 of the humeral anchor 104 or the proximal plate 205 of the humeral anchor 204 are rotated before implantation such that the apertures 116, 216 on the proximal plate 105, 205 are oriented toward a fracture L1, L2. In this context, the proximal plate 205 can include the proximal end 221 of the proximal portion 208 of the humeral anchor 204. By providing three apertures 216 in the proximal end 221 the advancement of the threads 224 need not advanced more than one-third of a turn beyond a position where sufficient securement of the proximal portion 208 is provided in the bone beneath the face R. In the embodiment illustrated in FIG. 11A-C, one of the screws 120 is advanced through one of peripheral apertures 116 or 216 located on a medial side of the humerus H and the central screw 140 may be advanced through a central aperture 136 or 236 and into the inferior portion i of the humerus on a lateral side of the humerus. The central screw 140 also can be advanced through the fracture L1, including advancing a distal threaded portion of the central screw 140 to a location within the inferior portion i of the humerus H such that the distal threaded portion 142 engages cortical bone but does not protrude through cortical bone of the inferior portion into the soft tissue adjacent to a lateral side of the humerus H (as illustrated in FIG. 4). Additional screws 120 can be advanced through peripheral apertures 116 or 216 located on anterior and posterior sides of the humerus H. In another embodiment, the first screw 120 is advanced toward a tuberosity "t", e.g., a greater tuberosity of the humerus H. In another embodiment, an additional screw 120 is advanced through another peripheral aperture 116 or 216 and toward a lesser tuberosity of the humerus H. Having screws that are advanced towards different parts of the humeral head advantageously ensure that the fracture L1, L2 is fixated at multiple sites, thereby reducing micro-movements at the fracture line and promoting faster healing of the fracture L1, L2.

In the illustrated embodiment in FIG. 11A, the fracture L2 additionally includes a fractured piece of the tuberosity t that is completely separated from the superior portion s at a tuberosity fracture line L2. In one method of repairing this fracture, a screw 120B is advanced through an aperture 116, 216 until a distal portion of the screw 120B extends through an exposed face of the tuberosity t at the fracture line L2.

Figure 8:
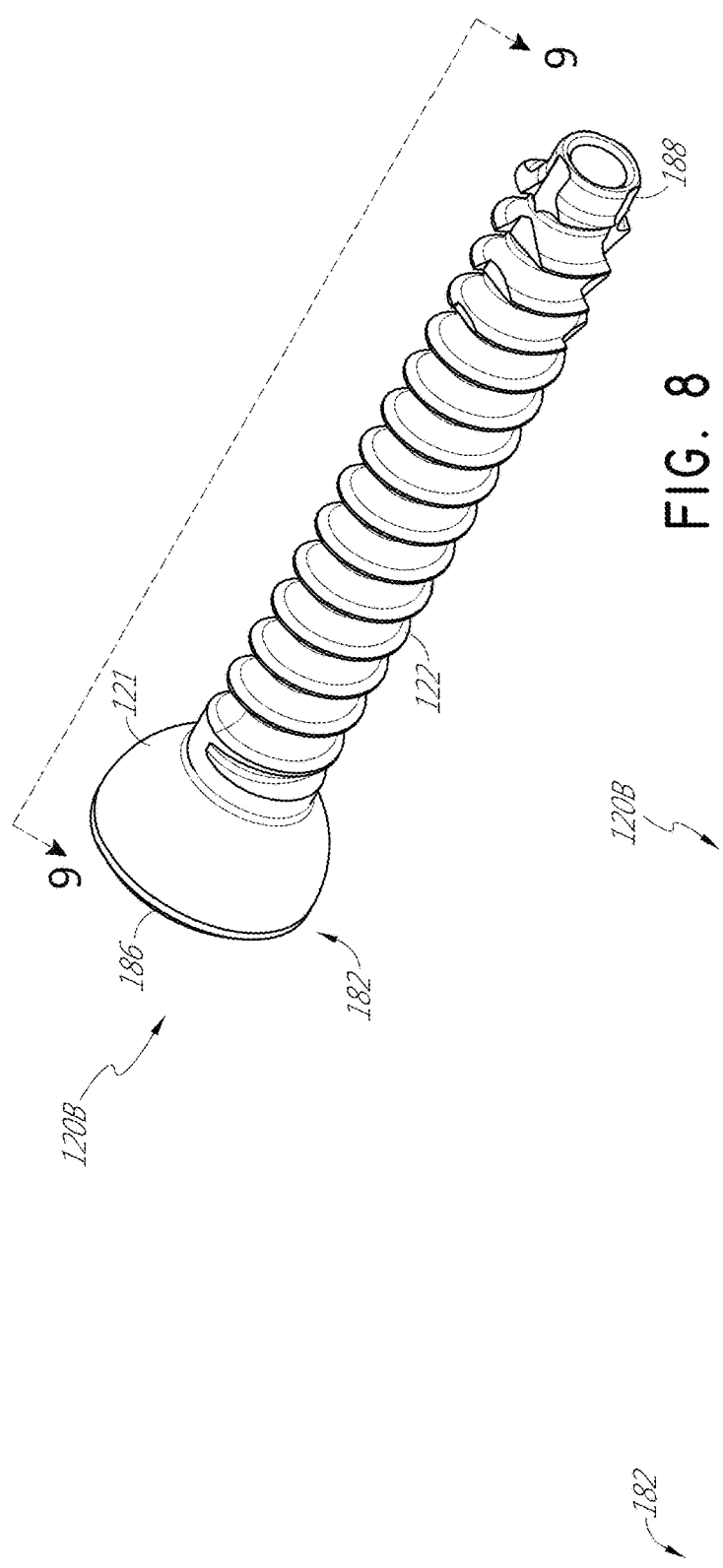
FIG. 8 is a perspective view of another embodiment of a screw that can be coupled with a humeral anchor and that is adapted to anchor soft tissue or bone to the humerus.
Figure 9:
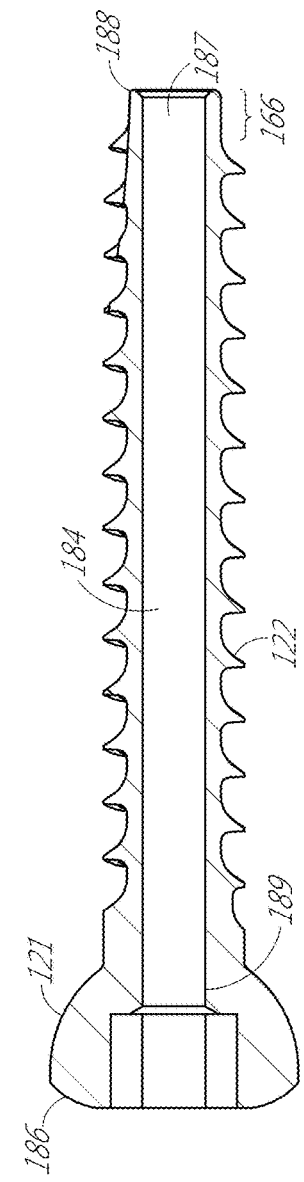
FIG. 9 is a cross-sectional view of the screw of FIG. 8.

FIGS. 8-10 illustrate embodiments of the screw 120B and assemblies including the screw 120B that can be used in the method of FIGS. 11A-11C. The screw 120B is adapted for fixating the fractured piece of tuberosity t to the humerus H, described above. The screw 120B includes features of the screw 120, such as the spherical part 121 of a proximal head 182 thereof. The proximal head 182 includes the substantially spherical surface 121. The screw 120B also includes the threaded portion 122 and a non-threaded distal portion 166 on a distal end 188. As shown in FIG. 9, the screw 120B has a lumen 184 extending between the proximal head 182 and the distal end 188.

The screw 120B can be used in combination with a suture anchor assembly 400. The suture assembly 400 includes a suture anchor 404 and a suture 408 that extends from a proximal end of the suture anchor 400, as shown in FIG. 10. The suture 408 of the suture anchor assembly passes into an aperture 187 at the distal end 188 of the screw 120B into and through the lumen 184 and exits the lumen 184 through an aperture 189 disposed in the proximal head 182 of the screw 120B. The suture anchor 404 is disposed distally of the distal end 188 of the screw 120B.

FIG. 11B illustrates a distal end of the suture anchor 404 being fixed to the fractured piece of tuberosity t. The suture 408 can be pulled through the lumen 184 of the screw 120B as illustrated in FIG. 10, thereby retracting the fractured piece of tuberosity t towards the tuberosity fracture line L2. FIG. 11C illustrates pulling the suture 408 under tension to hold the fractured piece of tuberosity tin compression against the superior portion s of the humerus at the tuberosity fracture line L2. As discussed earlier, the compression force not only provides fixation of the fractured piece of tuberosity t with the superior portion s of the humerus, but also stimulates bone growth at the tuberosity fracture line L2. Loose ends of the suture 408 may be tied using standard knot-tying or other suture fixation techniques. For example, the loose ends of the suture 408 may be tied to another suture strand pre-threaded through the anchor feature 300 or 304 of the humeral anchor 104 or 204 before the humeral anchor 104 or 204 was implanted.

Soft Tissue Anchoring

The stemless humeral anchors 104 and 204 can have additional features adapted for providing soft tissue or suture anchoring. For example, the anchor feature or apertures 300 or 304 shown in FIG. 17 allows a suture tied to a piece of bone or soft tissue to be pre-loaded before the humeral anchor 104 or 204 is implanted. In another embodiment, a loose suture alone may be pre-loaded through the anchor feature 300 or 304 such that the loose suture may be tied after implanting the humeral anchor 104 or 204 to another suture that is fixed to a piece of bone or soft tissue. In another embodiment, the loose suture can be threaded through a piece of bone or soft tissue using a standard suture passer, e.g. a needle, to fix the bone or soft tissue after the humeral anchor 104 or 204 has been implanted.

In some embodiments, the suture used for coupling the piece of soft tissue with the humeral anchor or with the screw is a pledgeted suture comprising a suture and a pledget or buttress between the suture and the soft tissue. The pledget minimizes a possibility of the suture strand loosening and/or tearing through tissue due to "cheese wire" effect.

Figure 5:
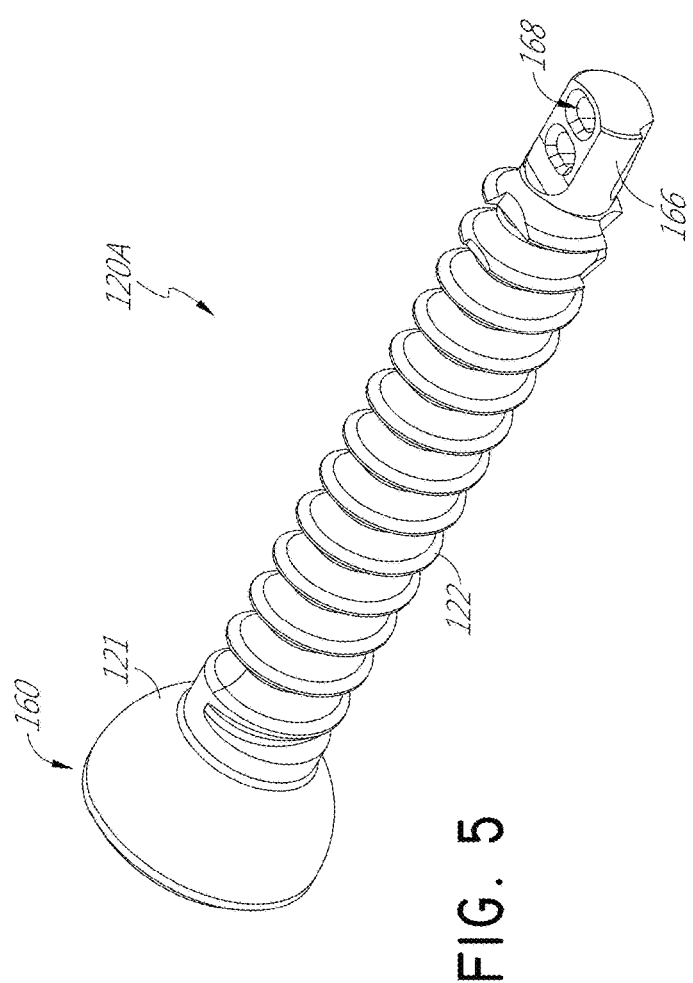
FIG. 5 is a perspective view of an embodiment of a screw with anchor features disposed on a distal portion thereof.
Figure 6:
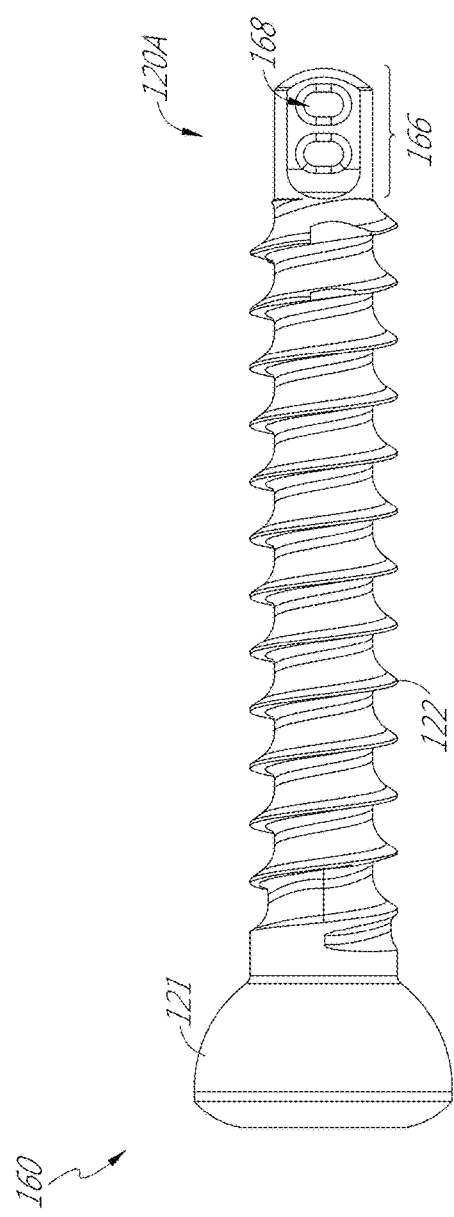
FIG. 6 is a side view of the screw of FIG. 5.
Figure 7:
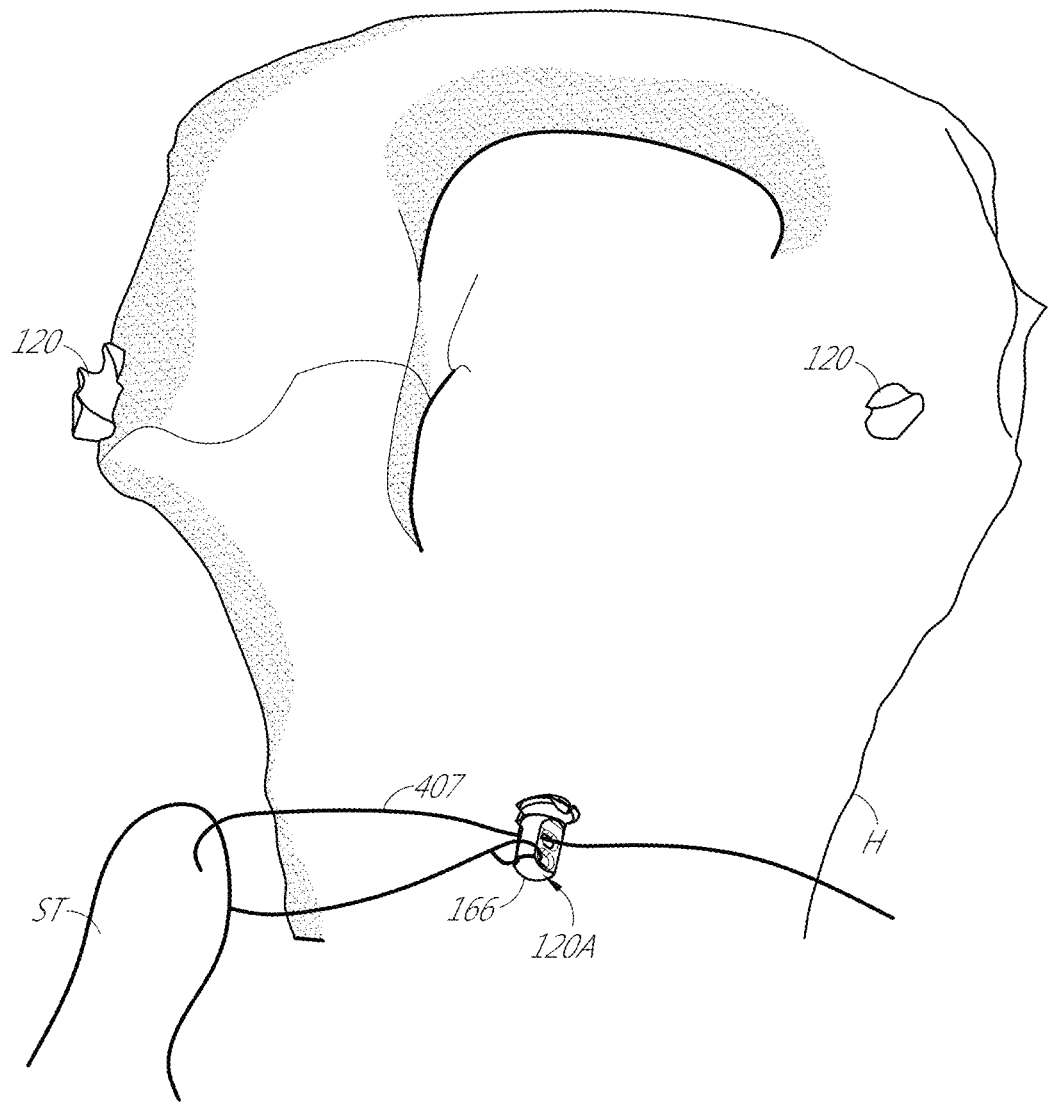
FIG. 7 is a view of the lateral side of the humerus, showing the screw of FIG. 5 protruding through a cortical bone portion of the humerus and a suture threaded through the anchor features to secure soft tissue to the bone.

FIGS. 5-7 illustrate another non-limiting embodiment of a screw 120A that is adapted for soft tissue or suture anchoring. The screw 120A includes features of the screw 120, such as a proximal head 160 including a substantially spherical surface 121 and a threaded portion 122. The screw 120A also includes an unthreaded distal portion 166. The unthreaded distal portion 166 of the screw 120A additionally includes at least one aperture or anchor feature 168. The one or more anchor features 168 can receive a suture before or after the screw 120A has been implanted. In an embodiment illustrated by FIG. 7, the screw 120A can be advanced into the humerus H until the unthreaded distal portion 166 penetrates and exits from a surface of a humerus H after the screw 120A has been advanced through cortical bone of the humerus H to reinforce the humeral anchor 104 or 204. A suture 217, e.g. a pledgeted suture, that is secured to a piece of soft tissue ST or bone fragment can pass through the anchor feature 168 and be tied either to the anchor feature 168 or at another location, thereby holding the soft tissue ST against the humerus H. In one embodiment, the soft tissue ST comprises a ligament, tendon or muscle, e.g. the rotator cuff tendons. The screw 120A may aid in rotator cuff repair. In another embodiment, the bone fragment comprises a fractured piece of the humerus H and the screw 120A can also aid in fixating a loose piece of bone that has broken off from the humerus H. In an embodiment of the screw 120A comprising a plurality of anchor features 168, the suture 217 can loop through more than one of the anchor features 168 to reduce a possibility of suture sliding or loosening.

One of ordinary skill in the art may appreciate from the disclosure herein that the suture anchor 404 in FIG. 10 can be coupled with soft tissue ST so that the screw 120B shown in FIGS. 8-10 can also be used for soft tissue or suture anchoring. After the suture has been pulled taut and before the screw 120B is implanted into bone, a loose end of the suture, that is, the end of the suture that is not fixed to soft tissue ST, can be looped through the lumen 184 of the screw 120B at least once. The screw 120B can then be advanced through the bone to fix the suture.

Figure 19:
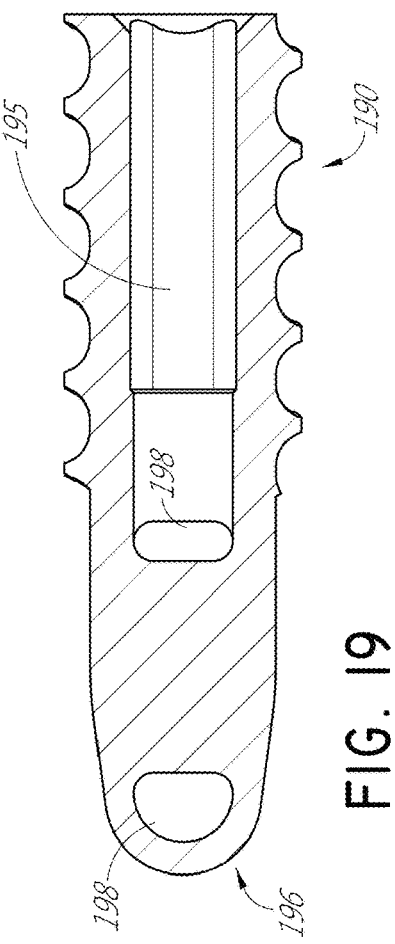
FIGS. 18 and 19 show views of a suture anchor having a blunt, atraumatic distal tip.
Figure 18:
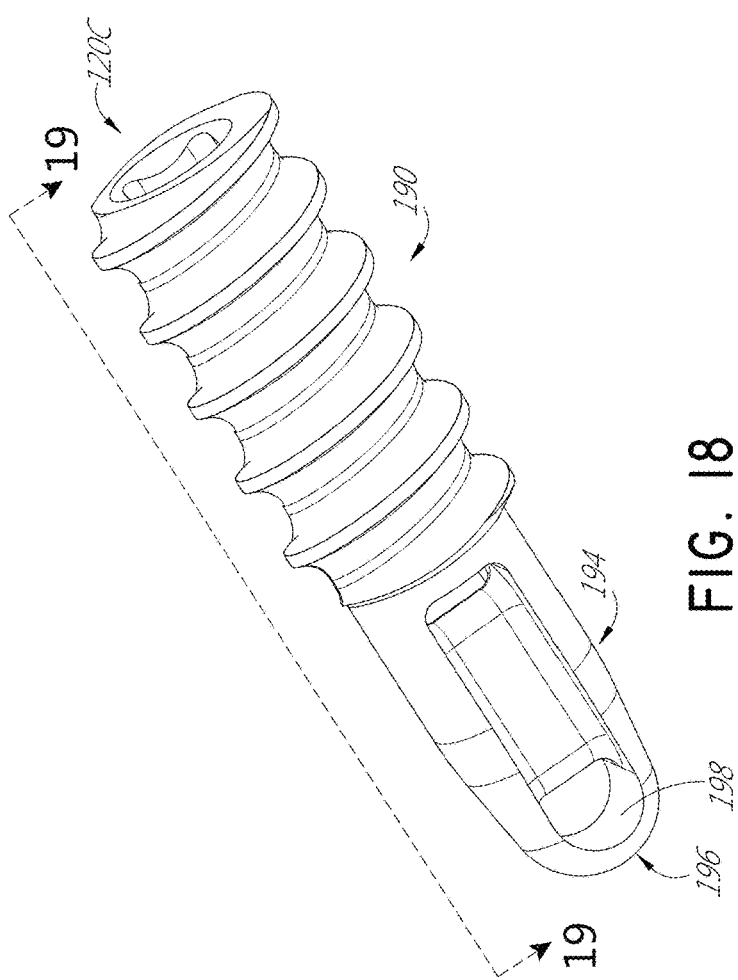

FIGS. 18-19 illustrates a distal portion of another non-limiting embodiment of a screw 120C. In this embodiment, the distal portion of the screw 120C includes a threaded portion 190 and an unthreaded distal portion 194 having at least one aperture or anchor feature 198 and a blunt, atraumatic tip 196. FIG. 19 shows that the screw 120C can include a lumen 195 that extends from a proximal portion to a least a portion of the threaded portion 190. The lumen 195 can be continuous with one of the anchor features 198. The screw 120C can replace the screw 120 or 140 and be used with the humeral anchors 104 or 204 and provides additional soft tissue and suture anchoring features that are a combination of the suture anchoring features of the screws 120A and 120B. Also, the structure of FIGS. 18 and 19 could be applied to the suture anchor 404 and used in combination with another screw, such as the screw 120B in the assembly 400.

Figure 20:
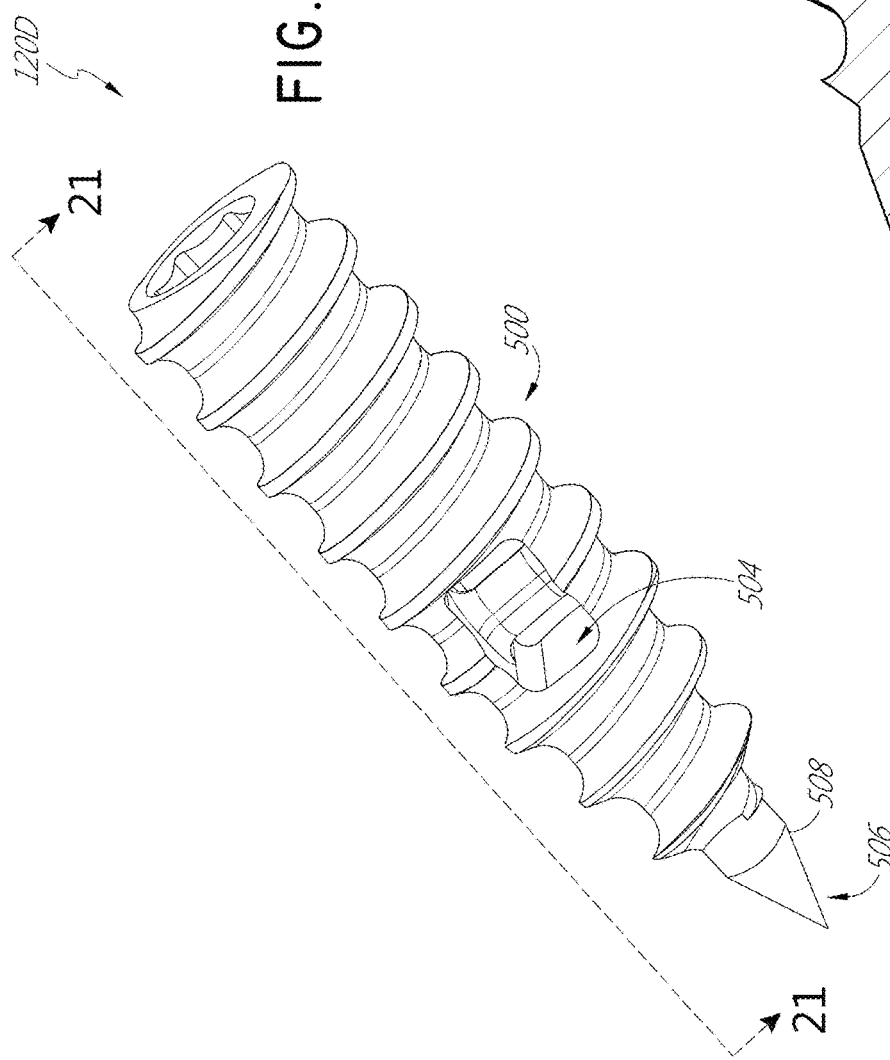
FIGS. 20 and 21 show views of a suture anchor having a pointed distal tip.
Figure 21:
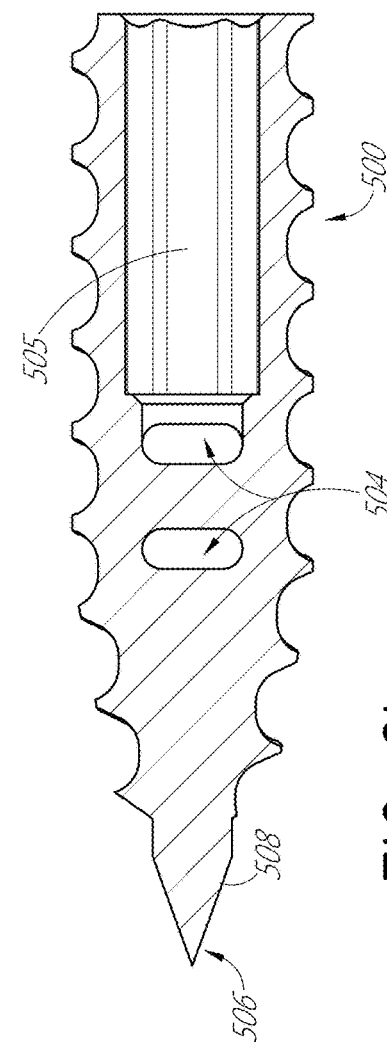

FIGS. 20-21 illustrate a distal portion of another non-limiting embodiment of a screw 120D. The screw 120D is similar to the screw 120C except that an unthreaded distal portion 508 of the screw 120D has a pointed tip 506. Also, an anchoring aperture 504 is located at a threaded portion 500 instead of the unthreaded distal portion 508. Like the screw 120C, the screw 120D has a lumen 505 extending from a proximal portion to at least a portion of the threaded portion 500 and the lumen 505 is also continuous with one of the anchor features 504. The screws 120D can also replace the screw 120 or 140 be used with the stemless humeral anchor 104 or 204 and provides additional soft tissue and suture anchoring features that are a combination of the suture anchoring features of the screws 120A and 120B. Also, the structure of FIGS. 20 and 21 could be applied to the suture anchor 404 and used in combination with another screw, such as the screw 120B in the assembly 400.

As used herein, the relative terms "proximal" and "distal" shall be defined from the perspective of the humeral shoulder assembly. Thus, distal refers the direction of the end of the humeral shoulder assembly embedded in the humerus, while proximal refers to the direction of the end of the humeral shoulder assembly facing the glenoid cavity.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A method for repairing a fracture of a humerus, the humerus having a superior portion superior to the fracture and an inferior portion inferior to the fracture, the method comprising:
    placing a stemless humeral anchor comprising a proximal plate at a face of the superior portion of the humerus, the stemless humeral anchor comprising an aperture providing access from a proximal side to a distal side thereof;
    advancing a screw through the aperture into the superior portion of the humerus;
    advancing the screw through the fracture into the inferior portion of the humerus.

2. The method of claim 1, where advancing the screw through the fracture includes advancing a distal threaded portion of the screw to a location within the inferior portion of the humerus such that the distal threaded portion engages cortical bone but does not protrude through cortical bone of the inferior portion into the soft tissue adjacent to the humerus.

3. The method of claim 1, wherein the inferior portion comprises a tuberosity of the humerus and wherein subsequently advancing includes advancing a distal portion of the screw through an exposed face of the tuberosity.

4. The method of claim 1, further comprising advancing a suture through bone or soft tissue and through one or more anchor features formed in the distal portion of the screw to secure the bone or the soft tissue to the screw.

5. The method of claim 1, wherein advancing the screw through the fracture separating a loose fragment of bone including the inferior portion from the superior portion and into cortical bone of the loose fragment to compresses the cancellous bone of the inferior portion against the cancellous bone of the superior portion at the fracture.

6. The method of claim 1, further comprising providing direct contact between a spherical surface of the screw and a spherical surface surrounding the aperture.

7. The method of claim 1, further comprising rotationally positioning a portion of the stemless humeral anchor including the plate relative to the humerus such that the aperture is oriented toward the facture.

8. The method of claim 1, wherein the aperture is disposed at the distal end of the stemless humeral anchor and further comprising advancing the screw through the facture into the inferior portion disposed inferior to a neck of the humerus.

9. The method of claim 1, wherein the aperture is a central aperture and the screw is a first screw and further comprising advancing a second screw through a second aperture that is disposed peripheral to the central aperture.

10. A surgical method, comprising:
 exposing a prosthetic shoulder joint comprising an anatomical configuration or a reverse configuration;
 removing a first articular component comprising a convex surface corresponding to an anatomic configuration or a concave surface corresponding to a reverse configuration to expose a stemless humeral anchor;
 advancing a first screw through a first aperture of a plurality of peripheral apertures disposed about the stemless humeral anchor and into bone of the humerus;
 advancing a second screw through a second aperture of the stemless humeral base and into cancellous bone of the humerus to enhance security of the stemless humeral anchor in the humerus; and
 coupling a second articular component after advancing the first screw and the second screw into the bone through the stemless humeral anchor.

11. The method of claim 10, further comprising advancing the second screw into a second peripheral aperture of the stemless humeral anchor.

12. The method of claim 11, wherein the first screw is advanced toward a greater tuberosity of the humerus.

13. The method of claim 12, wherein the second screw is advanced toward a lesser tuberosity of the humerus.

14. The method of claim 10, further comprising advancing the second screw into a central aperture of the stemless humeral base.

15. The method of claim 10, wherein the first articular component comprises convex articular surface and the second articular component comprises a concave articular surface.

16. The method of claim 10, further comprising:
 advancing a distal portion of the first screw and/or the second screw through cortical bone to be exposed at a humeral surface opposite the resection surface of the humerus; and
 securing soft tissue or bone fragments to the distal portion of the first screw and/or the second screw.

17. The method of claim 16, further comprising advancing a suture anchor of a suture anchor assembly into the soft tissue or bone; and retracting a suture of the suture anchor assembly proximally through a lumen of the screw to draw the suture anchor up against a distal portion of the screw.

* * * * *